US006760620B2

(12) United States Patent
Sippens Groenewegen

(10) Patent No.: US 6,760,620 B2
(45) Date of Patent: Jul. 6, 2004

(54) NON-INVASIVE LOCALIZATION AND TREATMENT OF FOCAL ATRIAL FIBRILLATION

(75) Inventor: Arne Sippens Groenewegen, Burlingame, CA (US)

(73) Assignee: Resolution Medical, Inc., Chapel Hill, NC (US)

(*) Notice: Subject to any disclaimer, the term of this patent is extended or adjusted under 35 U.S.C. 154(b) by 56 days.

(21) Appl. No.: 09/808,728

(22) Filed: Mar. 14, 2001

(65) Prior Publication Data

US 2001/0056289 A1 Dec. 27, 2001

Related U.S. Application Data

(63) Continuation-in-part of application No. 09/611,179, filed on Jul. 6, 2000.
(60) Provisional application No. 60/200,965, filed on May 1, 2000, provisional application No. 60/189,610, filed on Mar. 15, 2000, and provisional application No. 60/189,611, filed on Mar. 15, 2000.

(51) Int. Cl.[7] .......................... A01N 1/39; A61B 5/0402
(52) U.S. Cl. .......................................... 607/5; 600/518
(58) Field of Search ................................ 600/508–510, 600/515–518; 607/5

(56) References Cited

U.S. PATENT DOCUMENTS

| | | | |
|---|---|---|---|
| 3,565,060 A | 2/1971 | Sipple | |
| 4,539,995 A | 9/1985 | Segawa | |
| 4,550,502 A | 11/1985 | Grayzel | |
| 4,721,114 A | 1/1988 | DuFault et al. | |
| 4,751,471 A | 6/1988 | Dunseath, Jr. | |
| 4,751,928 A | 6/1988 | Hallon et al. | |
| 4,852,572 A | 8/1989 | Nakahashi et al. | |
| 4,865,039 A | 9/1989 | Dunseath, Jr. | |
| 4,974,598 A | 12/1990 | John | |
| 5,054,496 A | 10/1991 | Wen et al. | |

(List continued on next page.)

FOREIGN PATENT DOCUMENTS

| | | |
|---|---|---|
| WO | WO 97/49143 | 12/1997 |
| WO | WO 98/08274 | 2/1998 |
| WO | WO 99/05962 | 2/1999 |

OTHER PUBLICATIONS

Bagliani et al., "Left Origin of the Atrial Esophageal Signal as Recorded in the Pacing Site" *PACE*–(1998 21(1):18–24.

Lesh et al., "Comparison of the Retrograde and Transseptal Methods for Ablation of Left Free Wall Accessory Pathways" *Journal of American College of Cardiology*, (1993) 22(2):542–549.

Linnenbank et al., "Choosing the resolution in AD conversion of biomedical signals" *Building Bridges in Electrocardiology*, van Oosterom et al., Eds., Proceedings of the XXIInd International Congress on Electrocardiology, Nijmegen, The Netherlands (Jun. 25–29, 1995) 3 pages total.

(List continued on next page.)

*Primary Examiner*—Jeffrey R. Jastrzab
(74) *Attorney, Agent, or Firm*—Townsend&Townsend& Crew LLP; Mark D. Barrish, Esq.

(57) ABSTRACT

Devices, systems, and methods for localizing and/or treating arrhythmias of a patient's heart, which are particularly useful for localizing focal atrial fibrillation, allow locating arrhythmogenic regions of a chamber of the heart using heart cycle signals measured from a body surface of the patient. Non-invasive localization of the ectopic origin or exit site allows focal, circular, and/or perimeter treatment to be directed so as to inhibit complex arrhythmias without having to rely on wide-spread and time consuming sequential searches and/or on massively invasive simultaneous electrocardial sensors. The invention recognizes that effective localization of these complex arrhythmias can be significantly enhanced by techniques and structures which separate heart cycle signals originating from differing chambers and/or regions of the heart tissue.

29 Claims, 19 Drawing Sheets

U.S. PATENT DOCUMENTS

| | | | |
|---|---|---|---|
| 5,146,926 A | | 9/1992 | Cohen |
| 5,311,873 A | * | 5/1994 | Savard et al. ............... 600/508 |
| 5,313,953 A | | 5/1994 | Yomtov et al. |
| 5,483,968 A | | 1/1996 | Adam et al. |
| 5,595,183 A | | 1/1997 | Swanson et al. ............ 128/697 |
| 5,609,158 A | | 3/1997 | Chan |
| 5,634,469 A | | 6/1997 | Bruder et al. |
| 5,724,984 A | | 3/1998 | Arnold et al. |
| 5,733,151 A | | 3/1998 | Edsall et al. |
| 5,772,604 A | | 6/1998 | Langberg et al. |
| 5,794,624 A | | 8/1998 | Kwong |
| 5,818,570 A | | 10/1998 | Urbanczyk |
| 5,840,038 A | | 11/1998 | Xue et al. |
| 5,891,049 A | | 4/1999 | Cyrus et al. |
| 5,908,393 A | | 6/1999 | Albrecht et al. |
| 6,038,476 A | | 3/2000 | Schwartz |
| 6,047,206 A | | 4/2000 | Albrecht et al. |

OTHER PUBLICATIONS

Marchlinski et al., "Magnetic Electroanatomical Mapping for Ablation of Focal Atrial Tachycardias" *PACE* (1998) 21:1621–1635.

Metting van Rijn et al., "High–quality recording of bioelectric events, Part 2: low noise, low–power multichannel amplifier design" *Medical & Biological Engineering & Computing* (1991) 29:433–440.

Metting van Rijn et al., "Patient isolation in multichannel bioelectric recordings by digital transmission through a single optical fiber" *IEEE Transactions on Biomedical Engineering* (1993) 40(3):302–308.

Metting van Rijn et al., "Amplifiers for bioelectric events: A design with minimal number of parts" *Medical & Biological Engineering & Computing* (1994) 32:305–310.

Meurling et al., "Non–invasive Assessment of Atrial Electrophysiology in AF–Influence of Posture Change" *Computers in Cardiology* (1998) 25:637–640.

Peeters et al., "Clinical application of an integrated 3–phase mapping technique for localization of the site of origin of idiopathic ventricular tachycardia" *Circulation* (1999) 99:1300–1311.

Potse et al., "Continuous localization of cardiac activation sites using a database of multichannel ECG recordings" *IEEE Trans. Biomed. Eng.* (Submission date 2000) 8 pages total.

Potse et al., "Software Design for Analysis of Multichannel Intracardial and Body Surface Electrocardiograms" *Software for Multichannel ECG Analysis* (Draft date 2000) 7 pages total.

Potse et al., "Influence of Chronic Myocardial Infarction on Exit Site Localization of Ventricular Tachycardia Using Paced Body Surace Mappaing" *Proceedings of IEEE Trans. Biomed. Eng.* (Draft date 2000) 3 pages total.

Rodefeld et al., "Global Electrophysiological Mapping of The Atrium: computerized three–dimensional mapping system" *Pacing and Clinical Electrophysiology journal* (1997) 20(9):2227–2236.

Sedaaghi, "ECG Wave Detection Using Morphological Filters" *Applied Sig. Process* (1998) 5:182–194.

Seitman, David T., "Body Surface Potential Map Presentations" *Proc of the N. Engl Bioeng Conf, 4$^{th}$, Yale Univ, New Haven, Conn*, (May 7–8, 1976). pp. 275–278.

SippensGroenewegen et al., "A radiotransparent carbon electrode array for body surface mapping during cardiac catheterization" *Proceedings of the Ninth Annual Conference of the IEEE Engineering in Medicine and Biology Society* (Nov. 13–16, 1987) Boston, MA,, 4 pages total.

SippensGroenewegen et al., "Body Surface Mapping of Ectopic Left and Right Ventricular Activation" *Circulation* 1990) 82(3):879–896.

SippensGroenewegen et al., "Body Surface Mapping of Ectopic Left Ventricular Activation" *Circulation Research* (1992) 71(6):1361–1378.

SippensGroenewegen et al., "Design and Clinical Application of a Body Surface Mapping Reference Data Base for Detailed Localization of Ventricular Tachycardia Foci in Patients Without Structural Cardiac Disease" from Shenasa M, Borggrefe M, and Breithardt G, (eds). *Cardiac Mapping*, Mount Kisco, NY, Futura Publishing Co., Inc., (1993) pp. 347–366.

SippensGroenewegen et al., "Localization of the Site of Origin of Postinfarction Ventricular Tachycardia by Endocardial Pace Mapping" *Circulation* (1993) 88(5):2290–2306.

SippensGroenewegen et al., "Value of body surface mapping in localizing the site of origin of ventricular tachycardia in patients with previous myocardial infarction" *J. Am. Coll. Cardiol.* (1994) 24(7):1709–1724.

SippensGroenewegen et al. "Current Role of On–Line Body Surface Mapping in Postinfarction Ventricular Tachycardia Localization Using Catheter Pace Mapping"; Yasui et al. (Eds.) "Advances in Body Surface Mapping and High Resolution ECG" *Proceedings of Satellite Symposium on Body Surface Mapping and High Resolution Electrocardiography, Yokohama*, (1994) 141–155.

SippensGroenewegen et al., "Body surface mapping during pacing at multiple sites in the human atrium" *Circulation* (1998) 97:369–380.

SippensGroenewegen et al., "Body Surface Mapping of Atrial Arrhythmias" *Journal of Electrocardiology* (Supplement) (1998) 31:85–91.

SippensGroenewegen et al., "Atlas of Paced Body Surface QRS Integral Maps for Localization of the Site of Origin of Postinfarction Ventricular Tachycardia" *Journal of Electrocardiology* vol. 27 Supplement, pp. 105–112.

SippensGroenewegen, A., "Database of Body Surface ECG P Wave Integral Maps for Localization of Leftsided Atrial Arrhythmias" (Draft dated 2000) pp. 1–27.

SippensGroenewegen et al., "Body Surface Mapping of Counterclockwise and Clockwise Typical Atrial Flutter: A Comparative Analysis With Endocardial Activation Sequence Mapping," To be published in *Journal of American College of Cardiology*, (Jun. 2000) pp. 1–35.

Tang et al., "Use of P Wave Configuration during Atrial Tachycardia to Predict Site of Origin" *Journal of American College of Cardiology* (1995) 26(5):1315–1324.

Waktare et al., "Optimal Lead Configuration in the Detection and Subtraction of QRS and T Wave Templates in Atrial Fibrillation" *Computers in Cardiology* (1998) 25:629–632.

Yoshida et al., "A Case of Successful Ablation of Ectopic Atrial Tachycardia whose Origin was Detected by Isopotential Mapping" *Respiration and Circulation* (1998) 46(7):717–721.

Hewlett Packard Product Brochure entitled "EAST™ 12–Lead ECG Monitoring" (1999) 2 pages total.

Lifeshirt.com "Vital signs online" (Mar. 30, 2000) http://www.lifeshirt.com/, 1 page total.

Meridian Medical Technologies, Inc. Internet Wire, "Meridian Announces U.S. Clinical Studies with Innovative Prime ECG™ Mapping System" (Mar. 30, 2000) http://www.internetwire.com/technews/me/me990588.dsl, 2 pages total.

Meridian Medical Technologies, Inc. Internet, "Cardiopulmonary Systems" (Mar. 30, 2000) http://www.meridainmeds.com/cardio.html, 2 pages total.

Meridian Medical Technologies, Inc. Internet, "Prime ECG™ The new standard of care in heart attack detection" (Mar. 30, 2000) http://www.meridianmeds.com/prime.htm, 2 pages total.

* cited by examiner

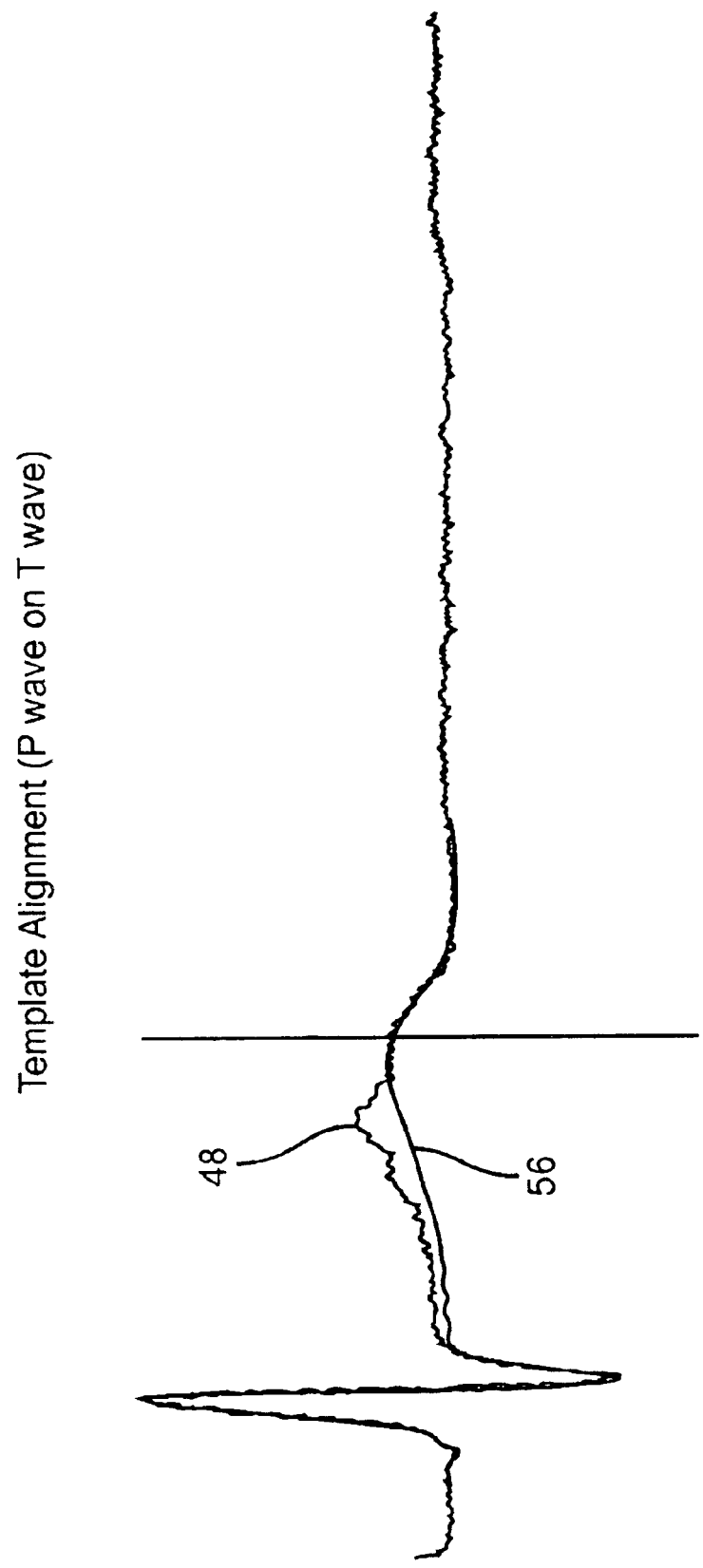

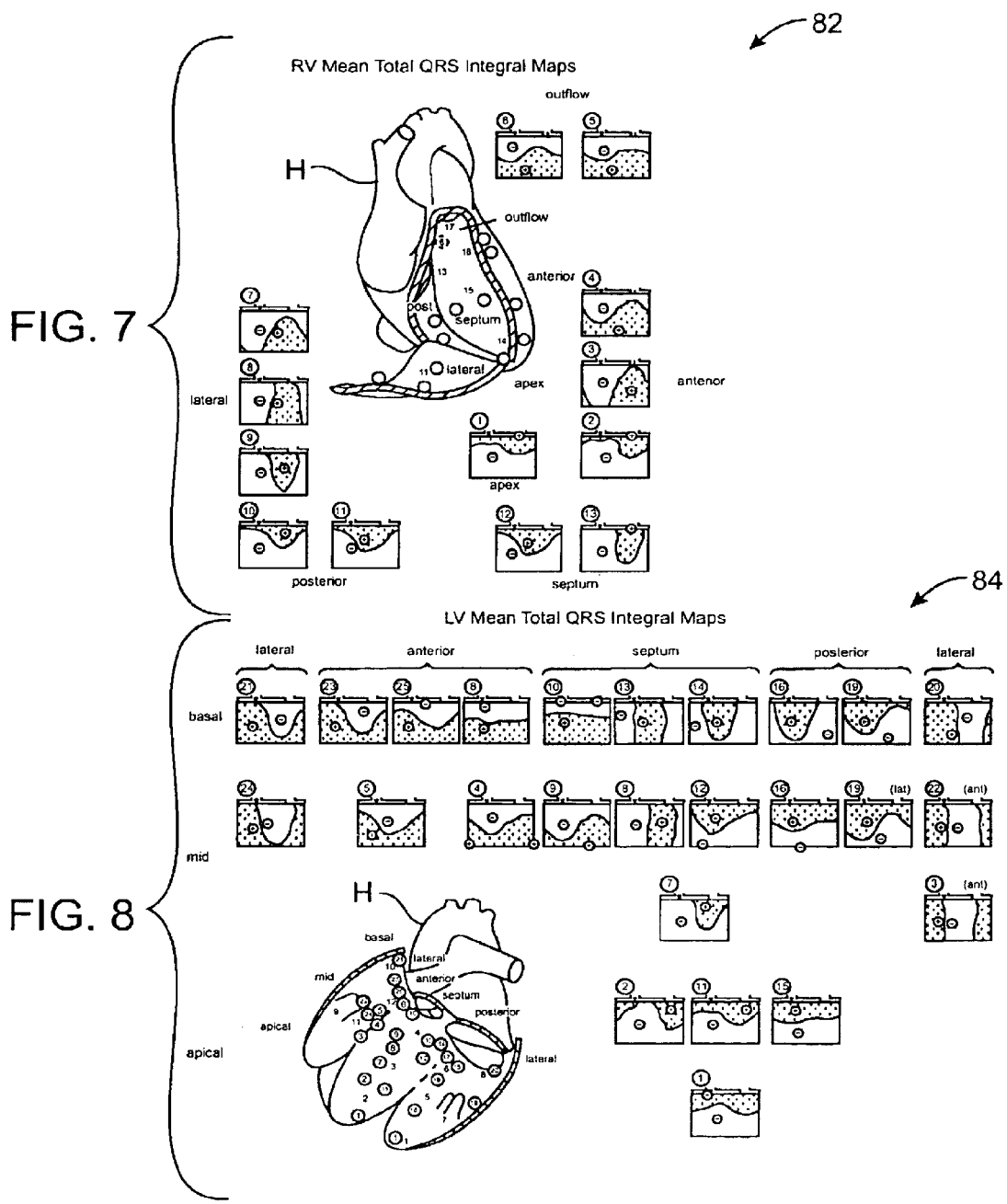

Skin Side

Top Side

Skin Side

Top Side

NON-INVASIVE LOCALIZATION AND TREATMENT OF FOCAL ATRIAL FIBRILLATION

CROSS-REFERENCE TO RELATED APPLICATION

This patent application claims priority from U.S. patent application Ser. No. 09/611,179 filed Jul. 6, 2000, and also claims priority from U.S. Provisional Patent Application No. 60/200,965 filed May 1, 2000; and U.S. Provisional Patent Application Nos. 60/189,610 and 60/189,611, both filed on Mar. 15, 2000. The subject matter of this application is related to that of concurrently filed applications entitled: Continuous Localization and Guided Treatment of Cardiac Arrhythmias, co-assigned with the present application, and QRST Subtraction Using an Adaptive Template for Analysis of T-Wave Obscured Atrial Activity; and is also related to that of U.S. patent application Ser. No. 09/724,947 filed Nov. 28, 2000, and U.S. Provisional Patent Application No. 60/196,204 filed Apr. 11, 2000, and No. 60/189,513 filed Mar. 15, 2000. The full disclosures of all of these applications are incorporated herein by reference.

BACKGROUND OF THE INVENTION

I. Field of the Invention

The present invention generally relates to devices, systems, and methods for diagnosing and/or treating of the heart. In a particular embodiment, the invention provides techniques for localizing and/or treating atrial fibrillation and other arrhythmias.

Significant progress has recently been made toward effective treatments of many cardiac arrhythmias. Contraction of a healthy human heart generally propagates through the heart tissue from the sinus node in the right atrium, and eventually the associated ventricles. This normal propagation of contraction forces blood to flow from the atria to the ventricles in a synchronized pumping action. Focal or re-entrant arrhythmias of the heart often originate at, and propagate from alternative heart tissue locations, resulting in irregular contractions of some or all of the heart tissues. Radiofrequency intracardiac catheter ablation of the alternative ectopic origin is now used to effectively treat a variety of arrhythmias, including ventricular tachyeardia (VT).

Although quite effective, current catheter ablation of arrhythmogenic sites has significant disadvantages. A particular challenge in an effective catheter ablation treatment is the time required for proper identification of the treatment site. As it is generally desirable to limit the size of the ablation, significant time is often spent testing candidate ablation sites. These candidate sites are often tested sequentially by positioning the intracardiac catheter against a site within (for example) the right ventricle, identifying the engaged tissue location within the ventricle, sensing and/or pacing the heart at the candidate site, repositioning the intracardiac catheter to a new candidate site, and repeating this process until the ectopic origin has been identified.

As fluoroscopy is often used to identify the location of the engaged tissue, this sequential iterative process can result in significant exposure of the patient and treating personnel to potentially harmful radiation. While alternative (and more complex) intracardiac catheter probe structures have been proposed to allow more rapid identification of the ectopic origin(s) of VTs and other focal arrhythmias, the size and cost of these complex structures may limit their acceptability, particularly for treatment of (for example) the left atrium of the heart, which is often accessed from the right atrium by a puncture through the atrial septum.

To overcome the disadvantages associated with these known time consuming and/or invasive intracardiac arrhythmia sensing and localization techniques, researchers have been working on alternative arrhythmia localization techniques which rely on body surfacing mapping often during pacing. Pacing often comprises initiating the arrhythmia by applying a small electrical pulse from a catheter. Electrocardiograms (ECG) may be recorded during abnormal atrial or ventricular activity and compared with ECGs taken during pacing at different sites within the heart, optionally using a standard 12-lead ECG system. More detailed information regarding ectopic sites can be obtained by recording heart cycle signals at the body surface using a more comprehensive sensor array. These heart cycle signals, which generally comprise small amplitude variations in electrical potential along the anterior and/or posterior torso, can be manipulated and/or mapped so as to provide an indication of the origin of the arrhythmia within the heart. Much of this work has concentrated on VT. More recent work has begun to investigate the possibility of localizing certain atrial arrhythmias, such as right atrial tachycardia. While the initial results of this research appear quite promising for treatment of selected individuals, significant advancements would be beneficial to allow widespread treatment of patients suffering from cardiac arrhythmias.

The most common form of cardiac arrhythmia may be atrial fibrillation (AFib). Atrial fibrillation is often paroxysmal in nature, which may contribute to the significant risks of the disorder. Atrial fibrillation may result in twice as many hospitalizations annually as VT, and may cause significant morbidity and/or mortality, leading not only to heart failure, but associated risks of thrombo-embolism and stroke.

Many current AFib patients are managed using antiarrhythmic drugs. Unfortunately, existing drug treatments are merely palliative, since they are aimed at suppression of the arrhythmia and not at curing the underlying disease. Many researchers are directing resources to development of therapeutic catheters to treat atrial fibrillation, attempting to build on several years of successful ablation for treatment of other arrhythmias. Early indications are that when accurately identified, ablation of ectopic origins of focal AFib may provide an effective treatment for the disorder. Hence, there would be significant benefits to extending the new body surface localization techniques to atrial fibrillation. The nature of AFib, however, represents a significant barrier to the direct application of known mapping techniques used with other arrhythmias.

Atrial fibrillation is generally more complex and difficult to localize than other arrhythmias. Focal AFib often exhibits an infrequent, irregular occurrence, and may be difficult to induce with known catheter mapping techniques. Even when atrial fibrillation is ongoing and/or successfully induced in the lab, AFib may exhibit prolonged occurrences in many patients, possibly requiring repetitive direct current shock cardioversion to convert the patient back into a normal sinus rhythm. Atrial fibrillation may also have multiple focal arrhythmia sources, possibly leading to detailed catheter mapping and unacceptably long procedures. Procedure times in general may be excessively long, particularly when conducted under prolonged fluoroscopic imaging, leading to excessive x-ray exposure to the patient, physician, and nursing staff. The current invasive options for AFib mapping also have significant disadvantages, particularly when they involve extended and/or traumatic catheter manipulation in the left atrium.

In light of the above, it would be desirable to provide improved devices, systems, and methods for localizing and/or treating AFib and other arrhythmias within a heart of a patient. The present invention provides such improvements, mitigating and/or overcoming at least some of the disadvantages of known approaches for diagnosing and treating arrhythmias.

II. Related Art

The following patents may be relevant to the subject matter of the present invention, and their full disclosures incorporated herein by reference: U.S. Pat. No. 5,311,873; and U.S. Pat. No. 5,634,469. Peeters, H. A. P., SippensGroenewegen, A. and others described "Clinical Application of an Integrated 3-Phase Mapping Technique for Localization of the Site of Origin of Idiopathic Ventricular Tachycardia" in *Circulation,* 99:1300–1311 (1999). SippensGroenewegen, A. et al. also described "Body Surface Mapping of a trial Arrhythmias: Atlas of Paced P wave Integral Maps to Localize the Focal Origin of Right Atrial Tachycardia", in *J. Electrocardiol.,* 31(Supp.):85–91 (1998). Related work was described by SippensGroenewegen, A. et al. in, "Value of Body Surface Mapping in Localizing the Site of Origin of Ventricular Tachycardia in Patients with Previous Myocardial Infarction", *J. Am. Coll. Cardiol.* 24:1708–1724 (1994). Each of these references is incorporated herein by reference.

SUMMARY OF THE INVENTION

The present invention provides improved devices, systems, and methods for localizing and/or treating arrhythmias of a heart. The techniques of the present invention are particularly useful for localizing atrial fibrillation, and allow locating arrhythmogenic regions of a chamber of the heart using heart cycle signals measured from a body surface of the patient. Non-invasive localization of the ectopic origin allows focal treatment to be quickly targeted to effectively inhibit these complex arrhythmias without having to rely on widespread and time consuming sequential searches, and/or on massively invasive simultaneous intracardiac sensor techniques. The invention recognizes that effective localization of these complex arrhythmias can be significantly enhanced by techniques and structures which separate superimposed heart cycle signals originating from differing chambers and/or regions of the heart tissue. In the exemplary embodiment, P wave signal portions are separated from superimposed QRST wave complex signals so as to isolate signals originating in an atrium from concurrent activity in the ventricle. The P wave signals may be measured by a thoracic array of electrical sensors distributed along the patient's skin across the torso. The invention allows invasive pace-mapping to be limited to a predetermined arrhythmogenic region within a particular chamber of the heart, often followed by ablation of the ectopic origin to inhibit the arrhythmia.

In a first aspect, the invention provides a method for treating fibrillation in a heart of a patient. The patient has an exposed body surface, and the method comprises measuring the fibrillation from the body surface. An arrhythmogenic region of the heart is located in response to the measured fibrillation. Treatment is directed at or near the arrhythmogenic region so that fibrillation is inhibited.

Preferably, heart cycle signals are sensed while no intracardiac probe is present in the heart, with the arrhythmogenic region being determined (at least in part) using the non-invasively sensed heart cycle signals. In many cases, an array having more than about 20 sensing locations will be coupled to thoracic skin of the patient. The sensed heart signals will often include signals originating in an arrhythmogenic chamber of the heart, superimposed with signals from other chambers. Typically, an atrial signal will be superimposed with a ventricular signal. These superimposed signals are separable by signal separators. The methods of the present invention often include separating the atrial and ventricular signals with such a signal separator.

In the exemplary embodiment of the present method, at least one reference cycle is selected from among a plurality of heart cycles measured by the sensor array. The arrhythmogenic region can be determined from the measured signals during this reference cycle, typically by selecting a time portion of the reference cycle, by integrating the separated signals from each sensor location within the selected time portion, and by arranging the resulting integral values within a data matrix according to the locations at which the signals are sensed along the body surface. Such a data matrix may be graphically plotted with the plots often including lines of constant integral values. These plots can be used to identify the arrhythmogenic region, most commonly by comparing the data matrix and/or plots to a database having a plurality of known arrhythmia cycles. Such databases will often have associated known arrhythmogenic regions for each known arrhythmia cycle.

Advantageously, the locating of the arrhythmogenic region can be performed using measurements of spontaneous fibrillation. The located arrhythmogenic region may have a surface area of less than about five square centimeters, often having an outer radius of less than about 2.5 cm, and ideally having an outer radius of about 1.0 cm or less. An ectopic site or exit site within such a limited arrhythmogenic region may be more precisely identified by subsequently introducing a mapping/pacing probe into the arrhythmogenic atrium. Alternatively, where locating can be performed to sufficient accuracy solely using the sensor array, ablation may directly proceed based on the non-invasively identified arrhythmogenic region. Such ablation will often be performed using radiofrequency energy, cryogenic cooling or electrosurgical energy, buy may alternatively be effected by focal or circular delivery of cryogenic cooling, ablative compounds, ultrasound energy, microwave energy, laser energy, or the like. Circular or perimeter lesions may be particularly beneficial for isolating arrhythmogenic regions in or near pulmonary veins and the like.

In another aspect, the invention provides a method for treating arrhythmia in a heart of a patient. The patient has an accessible body surface, and the heart has a left atrium, a left ventricle, a right atrium, and a right ventricle. Heart signals at the body surface include atrial signals superimposed with ventricular signals. The atrial and ventricular signals are separable by a separator. A database has information regarding a plurality of known arrhythmia cycles, each known arrhythmia cycle having an associated known arrhythmogenic region. The method comprises sensing signals during an arrhythmia initiation cycle from the body surface. Alternatively, one can also sense premature atrial beats with focal AFib, and/or persistent AFib. The atrial signals are separated from the sensed signals with the signal separator. An arrhythmogenic region (or in some embodiments, an insertion point of a concealed accessory pathway) of an atrium of the heart is located by comparing the separated signals to the database. A treatment is directed at or near an ectopic site or exit site within the arrhythmogenic region so that the arrhythmia is inhibited.

In another aspect, the present invention provides a system for treating arrhythmia in a heart of a patient. The patient has an accessible body surface and the heart has an atrium and a ventricle. A sensor array can be coupled to the body surface for sensing heart signals, the heart signals including atrial signals superimposed with ventricular signals. The atrial and ventricular signals are separable by a signal separator. A database includes information regarding a plurality of known cycles, each known arrhythmia cycle having an associated arrhythmogenic region. The system comprises a processor coupled to the sensor array and the database. The processor derives an arrhythmogenic region of the atrium from the heart cycle signals by separating the atrial and ventricular signals with the signal separator, and by comparing the separated signals to the database. A probe directs focal treatment at or near the arrhythmogenic region so that the arrhythmia is inhibited.

In yet another aspect, the invention provides a kit for use with a probe and a sensor array to treat arrhythmia in an atrium of a heart of a patient. The sensor array is coupleable to the body surface for sensing heart cycle signals. The probe has a treatment delivery surface. The kit comprises a processor coupleable with the sensor array. The processor generates an output in response to sensed heart cycle signals from the array. The kit also includes instructions for locating the arrhythmogenic region within the atrium by sensing the heart cycle signals from the body surface when no intracardiac probe is present in the heart, and by comparing the output of the processor with the database.

In yet another aspect, the invention provides a system for localizing an arrhythmia. The system comprises an input for body surface signals and a processor coupled to the input. The processor derives an arrhythmogenic region of a heart in response to the body surface signals. An output graphically indicates the arrhythmogenic region.

BRIEF DESCRIPTION OF THE DRAWINGS

FIGS. 3A–D graphically illustrate signal portion separation method steps employed by the program and method of FIG. 2.

FIG. 7 illustrates a database of QRS integral maps and associated ectopic origins within the right ventricle.

FIG. 8 illustrates a database of QRS integral maps and associated ectopic origins within the left ventricle.

DETAILED DESCRIPTION OF THE SPECIFIC EMBODIMENTS

While the following description is largely directed to localization and/or treatment of focal atrial fibrillation, the methods, devices, and systems of the present invention may be used for a variety of arrhythmias, including both focal and re-entrant arrhythmias (such as those resulting from scars). When used for treatment of re-entrant arrhythmia, treatment may be directed at or near an exit site or insertion point of a pathway. The invention is well suited for use with pulmonary vein isolation therapies now being developed (in which linear, circumferential, and/or perimeter lesions may isolate one or more pulmonary veins to inhibit propagation from triggers or exit sites in or near the veins) by allowing selection of target veins and/or indicating whether vein isolation should be utilized. The invention is particularly useful for localizing paroxysmal AFib, but may also find application for persistent and chronic AFib, localizing an insertion point of a concealed accessory pathway, and the like.

Figure 1A:
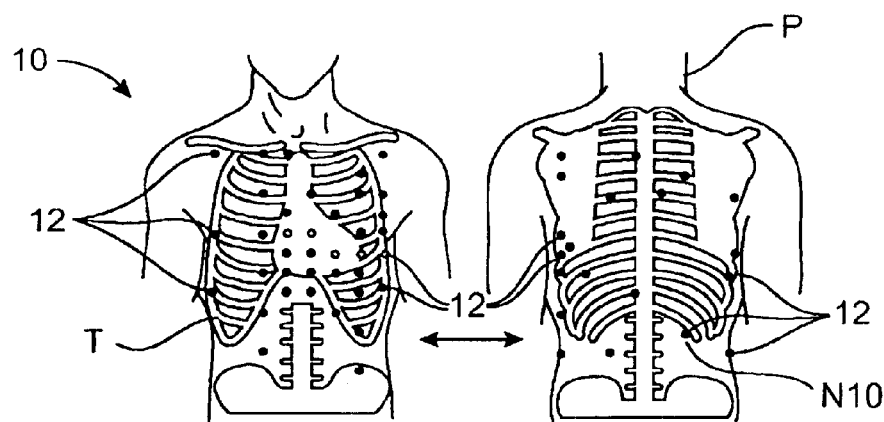
FIG. 1A schematically illustrates a sensor system having an array of sensing locations distributed across a patient's torso.

Referring now to FIG. 1A, the techniques of the present invention will generally make use of an array 10 of sensors 12 distributed across anterior and posterior skin surfaces of torso T on patient P. Array 10 provides multilead electrocardiogram (ECG) data at a plurality of sensing locations distributed across torso T, typically at over 20 sensing locations, more preferably at over 40 sensing locations, and ideally at 62 or more sensing locations.

Sensors 12 generally comprise unipolar or bipolar electrodes coupled to the patient's skin, or to an alternative accessible body surface (for example via a transesophageal approach) suitable for measuring electrical body surface potential. Suitable electrode structures may include those described in U.S. Pat. Nos. 5,311,873 and 5,634,496, previously incorporated herein by reference. Exemplary arrays for use in locations having large amounts of electromagnetic noise (such as an electrophysiology lab or other location in which electrosurgery or electrical stimulation of tissues for intracardiac pacing is performed) was described by Metting van Rijn, A. C. et al. in *IEEE Trans. Biomed. Eng.*, BME-40:302–308; (1993). Alternative sensor array structures and associated data acquisition and manipulations components were described by SippensGroenewegen, A. et al. in an article entitled, "Body Surface Mapping During Pacing at Multiple Sites in the Human Atrium: P wave Morphology of Ectopic Right Atrial Activation", *Circulation*, 97:369–380 (1998); and by Linnenbank, A. C. in a 1996 thesis for the University of Amsterdam entitled, "On-Site Recording, Analysis, and Presentation of Multi-channel ECG Data".

Figure 1C:
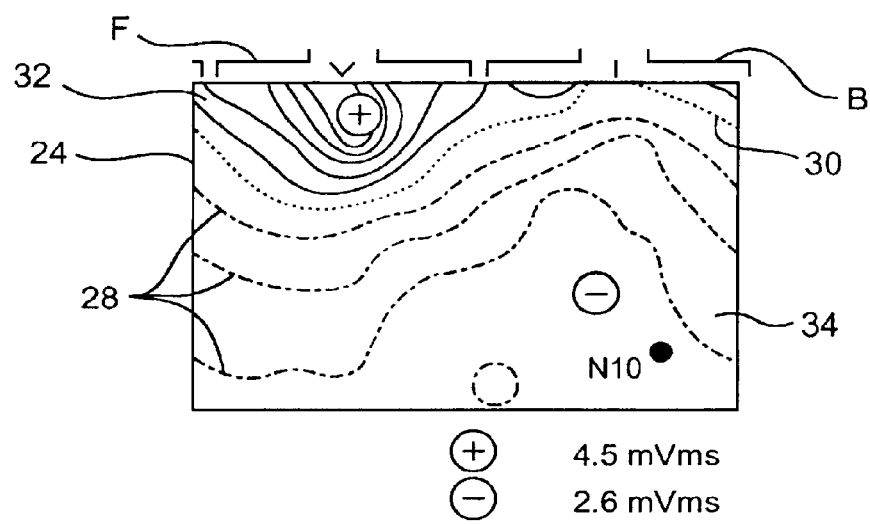
FIG. 1C illustrates a plot of a data matrix generated by mapping the integral values with positions corresponding to the locations of the sensors across the patient's torso.
Figure 1B:
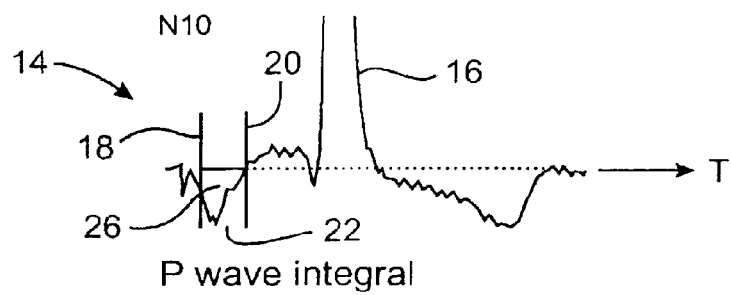
FIG. 1B graphically illustrates the method for calculating an integral value across a selected time portion of a heart signal cycle from a single sensor location.

Referring now to FIG. 1B, ECG data is preferably acquired simultaneously from each sensor 12 of array 10 at a sampling rate of over about 500 Hz, ideally at a sampling rate of about 1,000 Hz or more. In some embodiments, sequential sampling of sensor 12 from array 10 may alternatively be used, and higher or lower sampling rates are also feasible. When a lower sampling rate is used, the data may be upsampled using multi-rate filter banks.

Preferably, signals which are absent, for example, due to electrode obscurement by defibrillator patches or lead dislodgment, may be deleted. Poor quality signals may also be visually and/or automatically identified and rejected. Such rejected signals may be replaced using interpolation of adjacent lead recording data. Interpolation techniques may also be utilized to correct for offset variation among electrodes, and for linear baseline drifting.

Graph 14 includes an ECG signal tracing 16 representing the variation in voltage over time, as sensed by sensors 12, optionally at about 1 to 2 ms intervals. Signal tracing 16 may be used to evaluate heart cycle signals from the heart of patient P. In general, one or more reference heart cycles will be selected for manipulation and comparison. The reference heart cycle will typically be the heart cycle coinciding with initiation of the arrhythmia for localizing focal AFib, or a premature heart cycle that has the same morphology as the cycle that led to initiation of focal AFib. ECG Tracing 16 can be used to determine a beginning 18 and end 20 of a time portion 22 of the reference heart signal cycle which is of particular interest for evaluating one or more regions of the heart. In the example illustrated in FIG. 1B, a P wave onset may be determined by the time at which the voltage progresses beyond 30 $\mu V$ while termination of the P wave may be defined at the atrial J-point, as is generally understood in the field of electrocardiography. Alternative criteria for P wave onset and offset might also be utilized, and automated detection of time portion 22 is also feasible. Alternative time portions may also be selected.

Referring to FIGS. 1B and 1C, measurements made at each sensor 12 are preferably mapped onto a data matrix 24 according to the locations of the associated sensor. In the exemplary embodiment, a P wave integral numerical value 24 may be calculated based on heart cycle signals 16 within selected time portion 22 for a particular sensor location N10. This calculated P wave integral value reflects the time/ amplitude area of ECG signal at that sensor location within the selected time portion. Similar integral values are calculated for each sensor location, and the sensor values are mapped within data matrix 24 continuously from a portion of the data matrix associated with a front F of torso T, across a side of the patient P, and to a back B portion of torso T. As shown in FIG. 1C, the data matrix will often be presented graphically by calculating lines of constant integral values 28 based on the individual discrete integral values and their associated positions within the data matrix. In some embodiments, this information can be summarized by presenting a single line 30 of zero integral value between a region of positive integral values 32 and a region of negative integral values 34. In much of the description which follows, the region of positive integral values 32 is presented as a shaded region within a graphically depiction of data matrix 24. Exemplary alternative data matrices may be presented with shades of a first color (red, for example) for positive values, a second color (blue, for example) for negative values, and optionally a third color (such as green) for zero.

For localizing of certain arrhythmias, possibly including certain ventricular tachycardias and some types of atrial tachycardia, directly using measurements from sensors 12 to calculate integral values 26 for the selected time portion 22 maybe sufficient to identify an arrhythmogenic region (which may be relatively large) of a particular ventricle, and in some cases, a particular atrium. Localizing directly from the sensed heart cycle signals is significantly facilitated when the signals within the time portion of interest are predominantly indicative of activity within a candidate ectopic region of the heart. For example, when localizing ventricular tachycardia (VT), selecting a time portion dominated by the QRS complex in the signal can effectively localize arrhythmogenic foci or exit site, as more filly described in the *J. Am. Coll. Cardiol.,* 24:1708–1724 (1994), the full disclosure of which is incorporated herein by reference. This localizing of tachycardia foci within the ventricle may be facilitated by the domination of the QRS complex in the signal of the overall body surface potential.

Unfortunately, when localizing fibrillation foci within an atrium, the P wave (which can be indicative of activity within the atrium) will often be superimposed, either partially or completely, by the T-U wave. Physiologically speaking, the atrial activity of interest may coincide with ventricular recovery of the preceding cardiac cycle.

To accurately localize focal triggers during the initiation of paroxysmal or persistent AFib, the present invention makes use of systems and methods for effectively separating a signal portion of interest from a superimposed signal portion, with the two signal portions often being separated from a single signal sensed from at least one single sensor location. These signal separation techniques are particularly advantageous when used to isolate the P wave from a simultaneously occurring T-U wave. It may be possible in some circumstances to artificially separate these waves by active overdrive pacing using an intracardiac catheter with a pacing period selected to avoid superimposition of these two signal portions during artificially initiated arrhythmia. For the reason described above, non-invasive electrocardiographic localization of atrial arrhythmias, particularly atrial premature beats before or during invasive mapping procedures is highly advantageous. As will be understood with reference to FIGS. 2–3D, a QRST subtraction program helps to isolate and preserve the P wave morphology so as to enable trigger localization of focal AFib and other arrhythmias. The application of similar subtraction methodologies may also enhance the ability of body surface mapping systems to localize triggers, exit sites, pathway insertion points, flutter waves, and/or fibrillation waves of other atrial arrhythmias such as atrial flutter, chronic AFib, and the like. QRST subtraction program 40 may also enable application of inverse problem techniques to analysis of atrial arrhythmias, for example, when atrial depolarization is obscured by the preceding ventricular repolarization. It should be understood that alternative signal separation methods and systems might also be used, including those described in the following references, which are incorporated herein by reference: Slocum, J. et al., "Computer Detection of Atrioventricular Dissociation from Surface Electrocardiograms During Wide QRS Complex Tachyaardias," *Circulation,* 72:1028–1036 (1985); Slocum, J. et al., "Diagnosis of A trial Fibrillation from Surface Electrocardiograms Based on Computer-Detected Atrial Activity," *J. Electrocardial.,* 25:1–8 (1992); Holm, M. et al., "Non-Invasive Assessment of the Atrial Cycle Length During Atrial Fibrillation in Man: Introducing, Validating and Illustrating a New ECG Method," *Cardiovasc. Res.,* 38:69–81 (1998); Bollman, A. et al., "Frequency Analysis of Human Atrial Fibrillation Using the Surface Electrocardiogram and its Response to Ibutilide," *Am. J. Cardiol.,* 81:1439–1445 (1998); and Ingemansson, M. P. et al., "Autonomic Modulation of the Atrial Cycle Length by the Head Up Tilt Test: Non-Invasive Evaluation in Patients with Chronic Atrial Fibrillation," *Heart,* 80:71–76 (1998).

Figure 2:
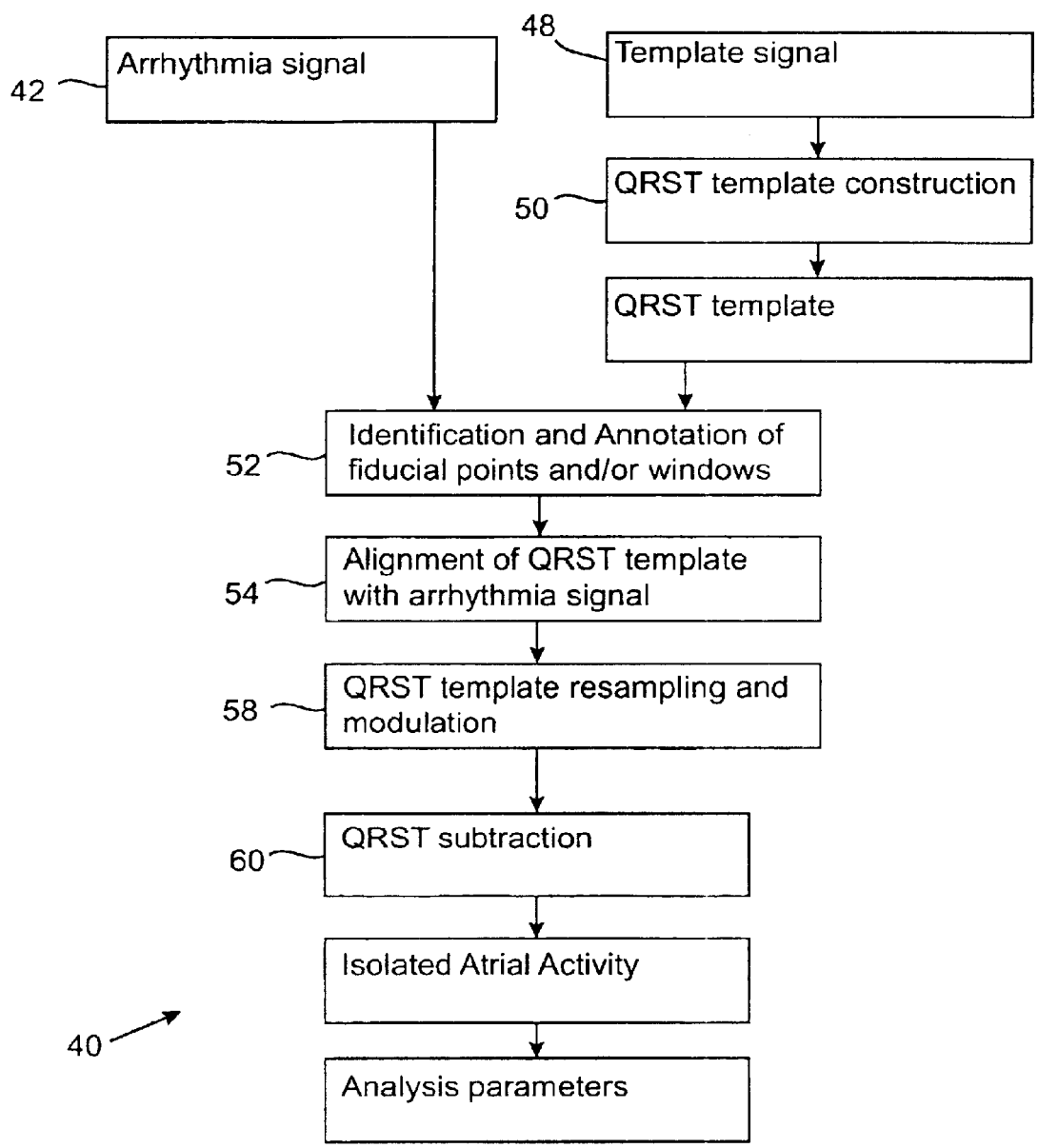
FIG. 2 schematically illustrates a method and computer program for separating a portion of an electrocardiogram signal relevant to a first portion of a heart from signals relevant to alternative portions of the heart.

Referring now to FIG. 2, automated QRST subtraction program 40 uses an adaptive QRST template constructed from averaged QRST complexes combined with ECG body surface measurements to enable isolation of the otherwise obscured ectopic atrial activity. Generally, this approach allows the surface ECG measurements to retain their intricate spatial and temporal detail within the P wave morphology. Subtraction program 40 is capable of unmasking and preserving subtle heart signal details of relatively low voltage P wave signal portions despite the obscuring superimposed relatively high voltage QRST complex. The QRST subtraction method of FIG. 2 is described in more detail in U.S. Patent Application No. 60/189,513 filed Mar. 15, 2000, previously incorporated herein by reference.

As described above, the method of program 40 generally includes recording of unipolar ECG data from the array of torso sites in step 42. The measured signal will include both the P wave (which is of interest for AFib) and a superimposed QRST signal portion 44.

Figure 3A:
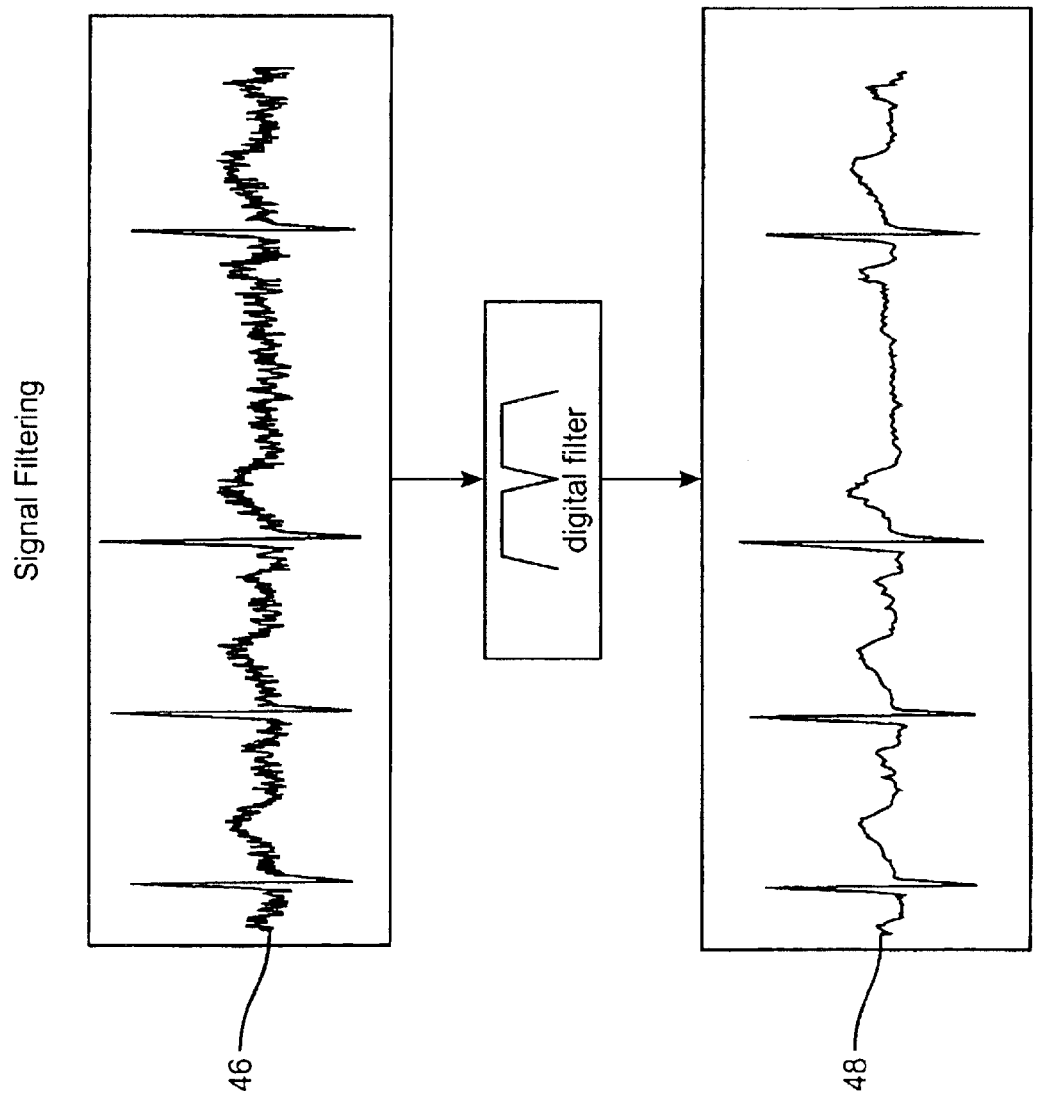

In the exemplary embodiment, about 100 cardiac cycles of 62-channel ECG data are measured during sinus rhythm or atrial overdrive pacing. Optionally, ECG signals can be acquired during both sinus rhythm and atrial pacing. Fewer cycles may be used if the spatial and temporal variations of the QRST complex are relatively low. Typically, more than ten (10) cycles will be used, often more than 50 cycles for construction of the QRST template. As illustrated in FIG. 3A, off-line digital filtering of the data designated for template construction may be performed using a 0.5 Hz high-pass filter, such as an IIR Chebychev Type-1 filter. This can help to correct for respiration-related baseline drifting. Additionally, a 100 Hz low-pass filter, such as a IIR Chebychev Type-1 filter, may be used to remove high-frequency signal artifacts. Additionally, a 50–60 Hz notch filter may be used to remove line-frequency interference. Similar filtering may be employed on the superimposed signals to be separated.

Each filtered QRS complex 48 may be identified using a complex-resonator/comb filter, together with a dual-edge threshold detection technique similar to that described by Ruha, A. et al., in an article entitled "A Real-Time Microprocessor QRS Detector System with a 1-ms Timing Accuracy for the Measurement of Ambulatory HRV", *IEEE Trans. Biomed. Eng.*, 44:159–167 (1997), the disclosure of which is incorporated herein by reference. Alternative QRS detection methods might also be used.

R wave fiducial points are marked and the average R-R interval is computed. The dominant QRS morphology is identified, optionally using visual identification from pooled data, automated statistical methods, or the like. This dominant QRS morphology is used to select complexes for template creation.

Figure 3B:
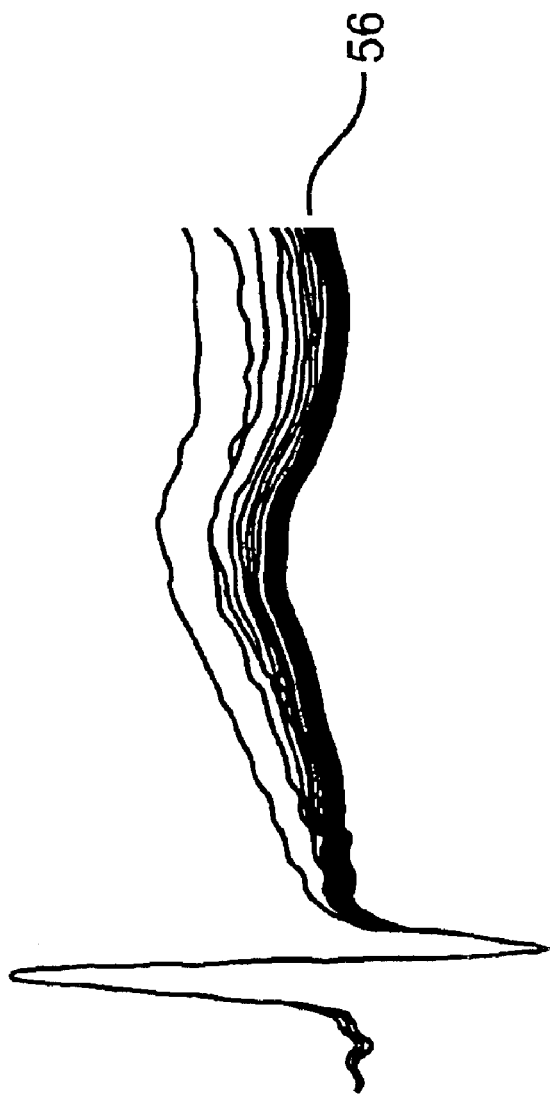

QRST template construction 50 may be understood with reference to FIG. 3B. The selection of complexes for template creation may be based on two criteria: QRS pattern, and R-R interval length.

Regarding QRS pattern criteria, complexes of each cycle are compared with the template using parametric crosscorrelations. In the exemplary embodiment, Pearson's coefficients are computed for a fixed time window sliding over a 20 ms time period. Once again, a variety of alternative cross-correlations may be used. Each newly selected complex (for example, those having $r \geq 0.98$) is aligned and averaged with previously selected cycles, and the QRS template is updated. Each complex which does not have adequate correlation with the template is excluded, with these complexes often being ectopic or aberrantly conducted ventricular beats.

Minimum R-R duration threshold is computed and only complexes having an R-R duration above the computed threshold are used to create the QRST template. For each complex, the Q wave fiducial point is identified and the average Q-R interval is computed. The average Q-T interval (the length of the QRST complex) is computed, optionally using a modified Bazett's formula. Additional correction for baseline drifting may be performed using linear interpolation after averaging a window prior to the Q wave. An adaptive template may be constructed from the selected complexes by averaging their QRST intervals, optionally with the complexes aligned by a window surrounding the R wave fiducial point.

In step 52, the above-described fiducial window in the QRS complexes, together with an additional fiducial time window around the peak of the T wave, are marked automatically. These fiducial windows are marked in both the QRST template, and in the superimposed signal 48 containing a QRST complex together with a superimposed P wave.

In step 54, the template 56 and the superimposed signals are aligned. Typically, T wave window onset for the template is estimated as 0.64*QT. The T wave window is adjusted for each complex based on the QT interval length. Optionally, the operator can manually adjust any fiducial marker, such as by manipulating a mouse, joystick, by putting a numerical value, or the like, the template's QRS fiducial points and T wave windows are aligned with the respective windows of the superimposed QRST complex. Alignment of superimposed signal 48 and template 56 may be performed manually, or automatically by sliding windows over each other in 10-ms increments and calculating cross-correlation coefficients.

Figure 3D:
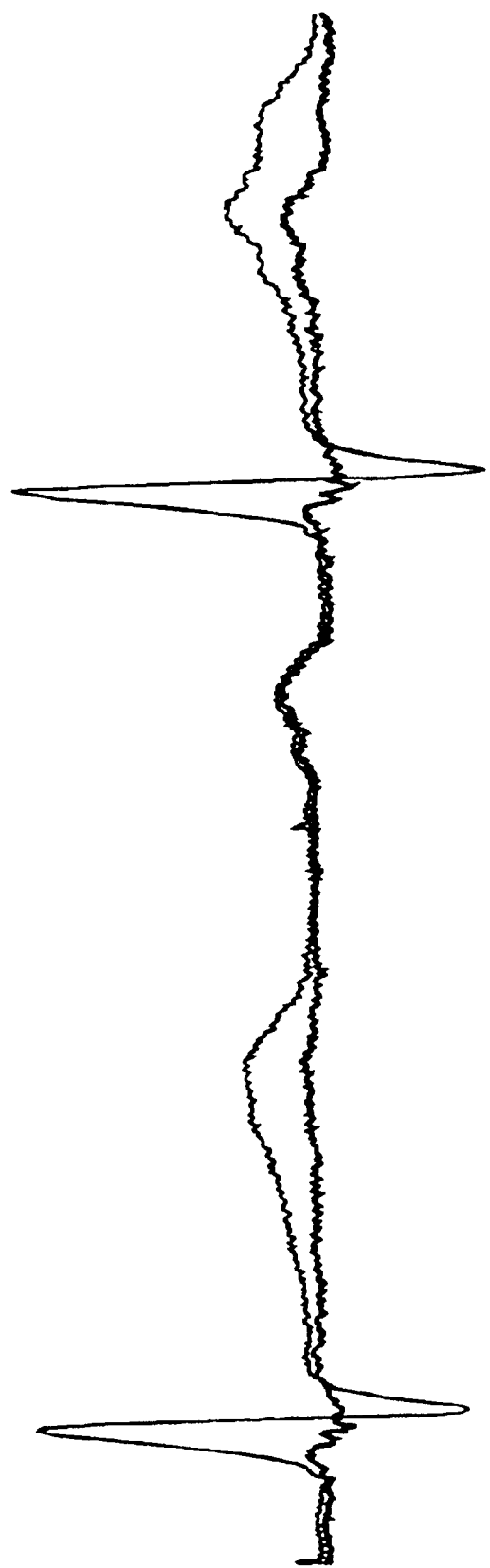

After alignment of the fiducial windows, the template is resampled as well as amplitude modulated 58, and then QRST subtraction is carried out as can be understood with reference to FIG. 3D and step 60. Template resampling and modulation are performed to compensate for discrepancies in duration (as a result of rate-related differences in the QRST interval) and amplitude (as a consequence of variations in peak R-T wave voltage, which may be predominantly caused by respiratory variation). This process is particularly geared toward obtaining optimal subtraction performance of the TU wave complex. Optionally, cubic spline interpolation methods may be used for template resampling, although other multi-rate processing methods can also be used.

The subtraction procedure from channel-to-channel may be performed according to electrode position. This facilitates maintaining sliding intervals as small as 10 ms while having the Q-T interval dispersion accessed in multiple leads. Additional low-pass filtering can be carried out to smooth possible QRS leakage after QRST subtraction. The remaining ECG signal after QRST subtraction features a P wave which is effectively isolated from the previously superimposed T-U wave.

After the QRST segment is effectively subtracted from each measured signal containing a P wave of interest, the morphology of the isolated P wave can be analyzed as described above. Specifically, an integral map may be computed of the separated, previously superimposed P wave. This integral map can be compared with a database of P wave maps created by pacing, so that atrial tachycardia, atrial accessory pathway insertion sites, and focal triggers of paroxysmal or persistent AFib may be localized using data from the surface ECG array 10, as shown in FIG. 1A. Advantageously, the method described herein above may obtain high performance in the T-U wave range by correcting specifically for differences in both the QRST duration, and in the voltage of the T wave. Additionally, the above-described QRST subtraction methodology makes use of a separate data set than the superimposed wave to be separated, with the separate data set optionally being obtained during sinus rhythm or atrial overdrive pacing to help insure that atrial and ventricular activity are clearly separated. As was also mentioned above, the superimposed wave or reference cycle of interest will often comprise a single ectopic atrial heartbeat which can be readily separated using the above-described method.

Once the signal separation has been successfully completed for the reference heartbeat at each sensor location 12 of array 10, a P wave integral map may be plotted from the data matrix 26 as described above with reference to FIGS. 1A–C. Similar QRS integral data matrices and plots may be generated for localizing ventricular arrhythmias.

Figure 4A:
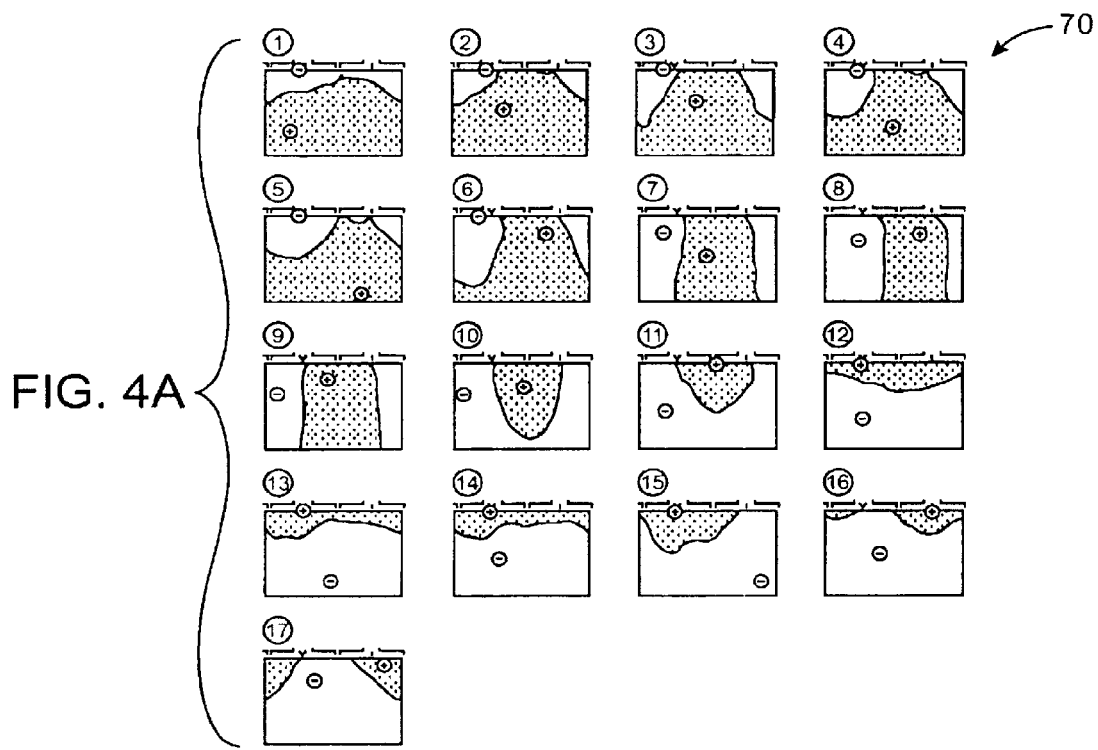
FIG. 4A graphically illustrates a database of known atrial paced heart cycles as 17 mean P wave integral maps.
Figure 4B:
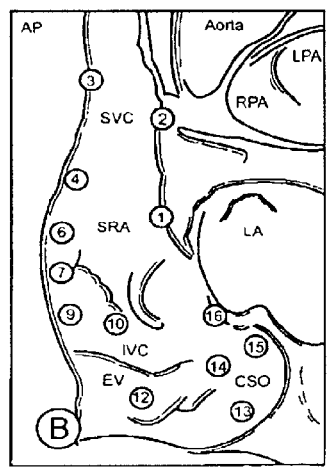
FIGS. 4B and 4C illustrate 17 known right atrial ectopic origins associated with the 17 mean P wave integral maps of FIG. 4A.
Figure 4C:
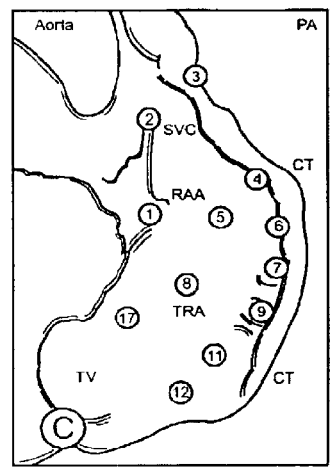

Referring now to FIGS. 4A–C, a graphical plot of a particular patient's P wave integral may be used to localize an arrhythmogenic region in an atrium by comparing the P wave integral plot for the patient to a database of P wave integral plots having associated known ectopic foci within the right atrium. Each of the 17 plots of database 70 has an associated ectopic region (identified by the encircled numbers illustrated in FIGS. 4B and 4C), the database having been gathered using pacing.

The anterior-posterior view AP shown in FIG. 4B and the posterior-anterior PA view of FIG. 4C illustrate the right atrial cavity. Anatomical landmarks included in these diagrams include the superior vena cava SVC, and inferior vena cava IVC; the right atrial appendage RAA; the smooth right atrium SRA; the trabeculated right atrium TRA; the crista terminalis CT; the fossa ovalis FO; the left atrium LA; the Eustachian valve EV; the coronary sinus os CSO; the tricuspid valve TV; the right pulmonary artery RPA; and the left pulmonary artery LPA.

Figure 5A:
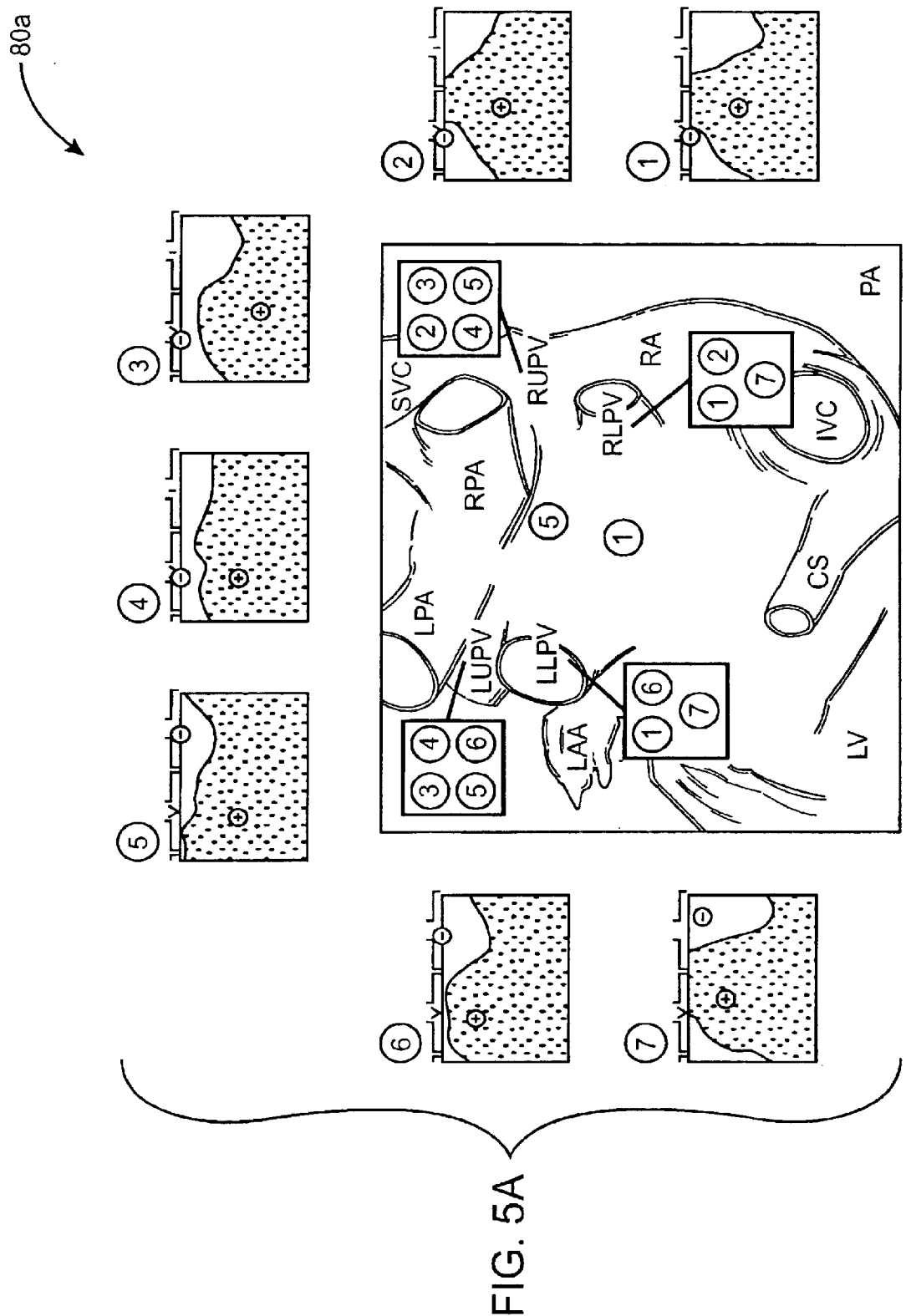
FIGS. 5A–C illustrate a database of mean P wave integral maps and associated locations of ectopic origins of the left atrium.
Figure 5B:
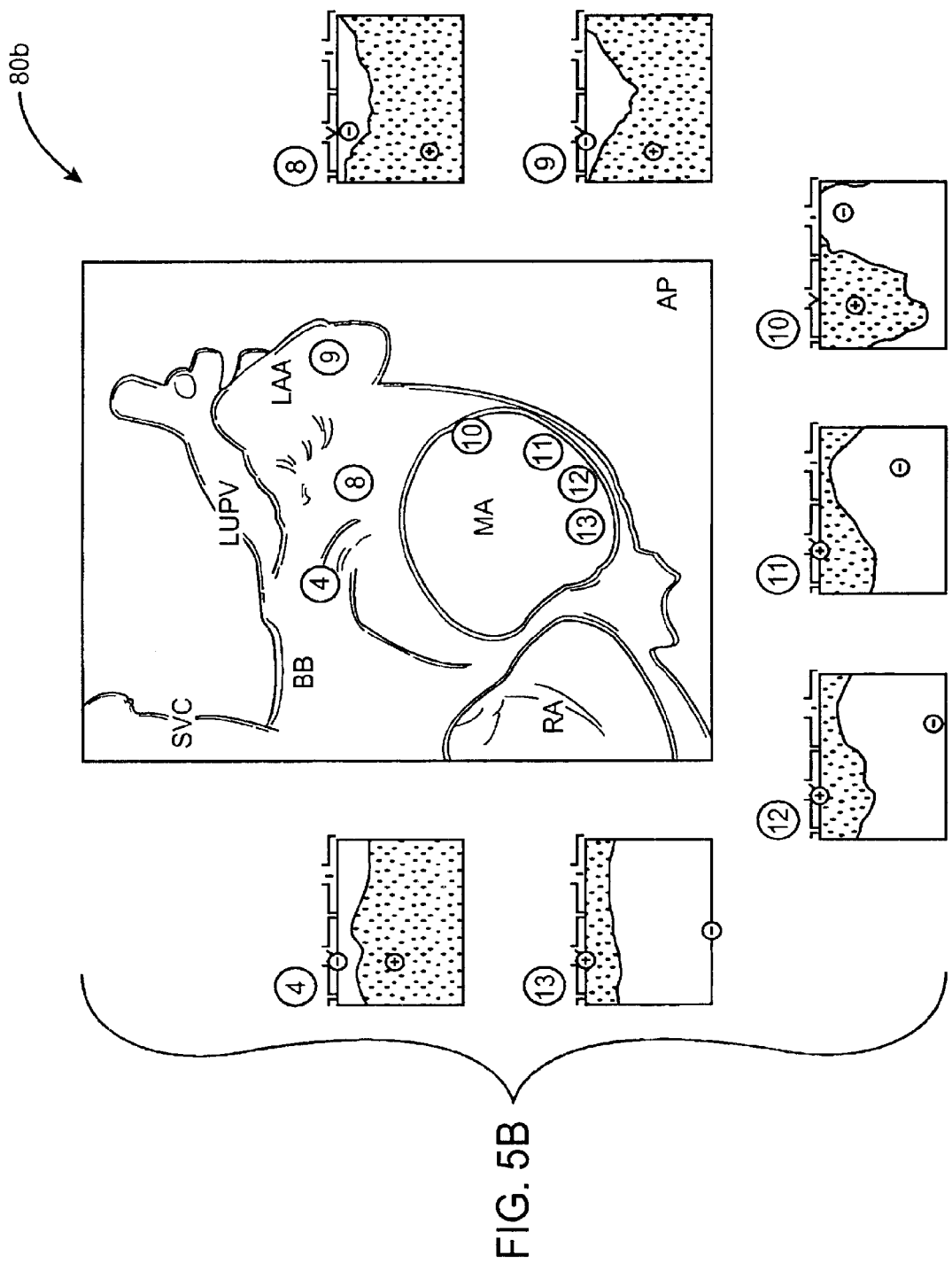
Figure 5C:
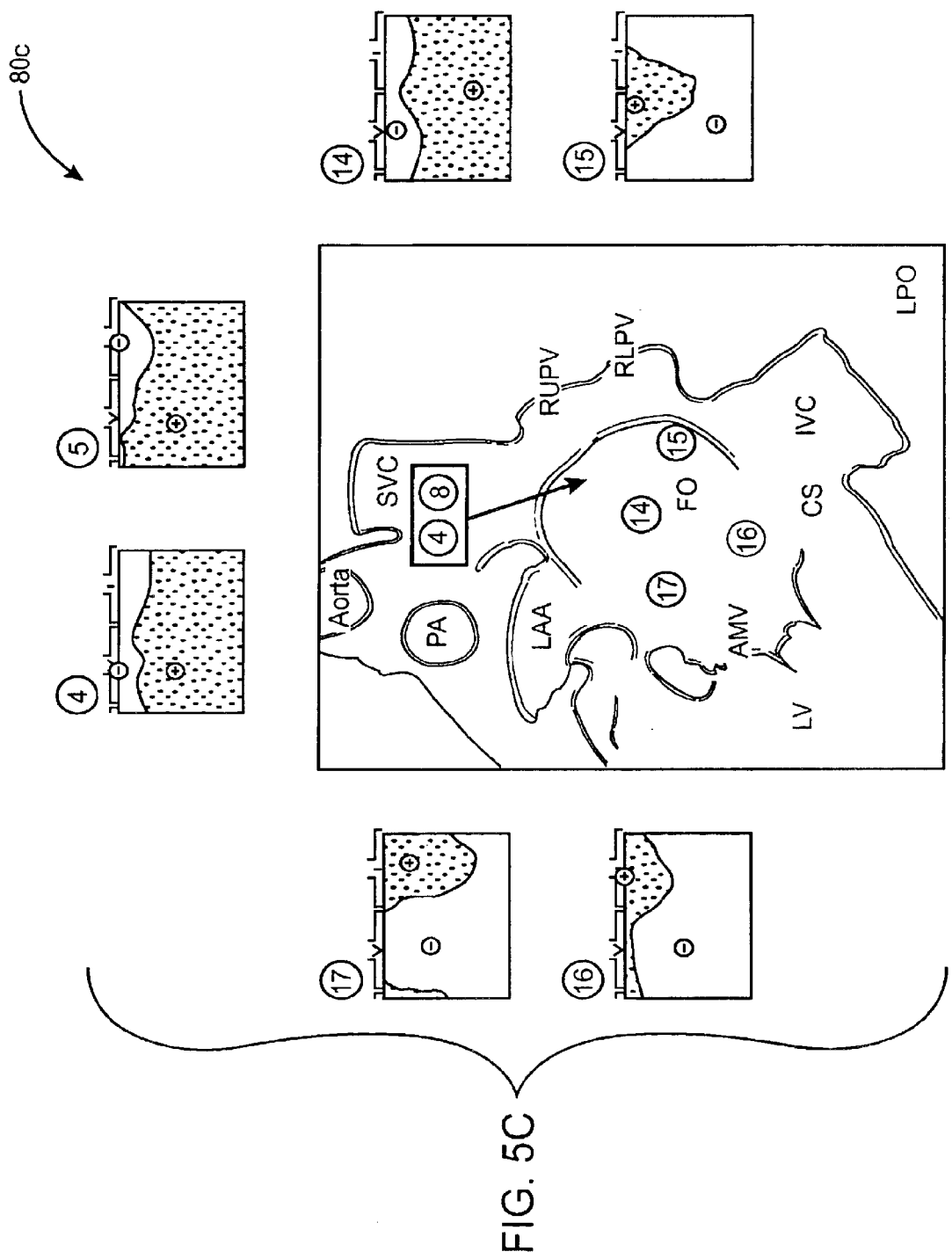
Figure 6A:
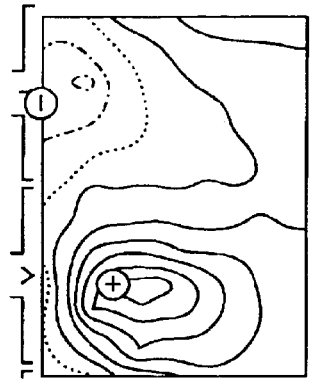
FIGS. 6A–F illustrate correlations between integral maps of paced heart signal cycles obtained in different patients at a common region in the left atrium.
Figure 6B:
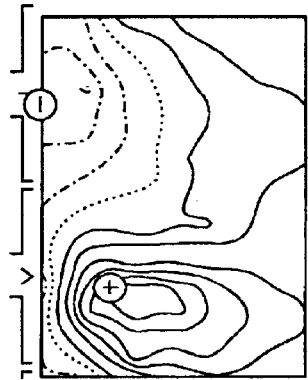
Figure 6C:
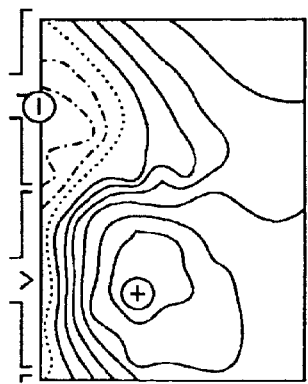
Figure 6D:
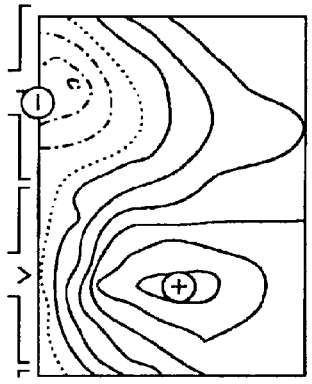
Figure 6E:
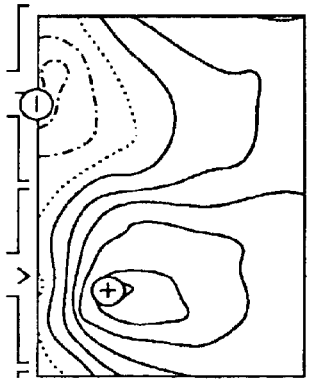
Figure 6F:
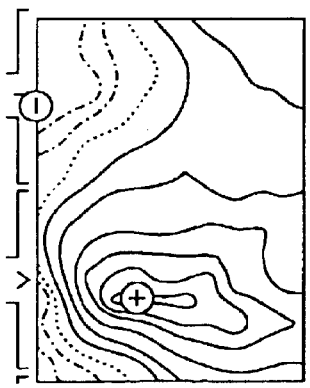

Methods for assembling a right atrial database are described in detail in the *J. Electrocardiol.*, 31 (Supp.) :85–91 (1998), previously incorporated herein by reference. A similar left atrial database 80a, b, and c (generally referred to as left atrial database 80) is illustrated in FIGS. 5A–C. Once again, the encircled numbers relate mean P wave integral plots to specific endocardial regions of pacing shown in the anatomical diagrams.

The mean P wave integral maps of left and right atrial databases 70, 80 feature extreme positions and zero line contours without positive and negative integral contour lines. Alternative plot formats, such as three-dimensional or chest anatomy-based formats, map displays using various color schemes, and the like, may also be used.

The anatomical diagrams illustrated in FIGS. 5A–C present a posterior-anterior PA view and anterior-posterior AP view, and a left posterior-oblique LPO view of the left atrium LA. Once again, major anatomical landmarks are highlighted including the left and right pulmonary arteries LPA, RPA; the superior and inferior vena cava SVC, IVC; the left atrial appendage LAA; the right atrium RA; the coronary sinus CS; the left ventricle LV; the left upper pulmonary vein LUPV; the left lower pulmonary vein LLPV; the right upper pulmonary vein RUPV; the right lower pulmonary vein RLPV; Bachmann's bundle BB; the mitral annulus MA; the anterior mitral valve leaflet AMVL; and the fossa ovalis FO.

Referring now to FIGS. 6A–F, six individual P wave integral maps included within group 6 were each obtained during pacing at the left upper and left lower pulmonary veins. These six similarly located pacing sites were grouped together within group 6 of left atrial database 80, and these plots were averaged to produce the sixth numbered mean plot of the left atrial database. The spatial compatibility of these patterns can be clearly seen, particularly with reference to the location and orientations of both the highest positive and negative integral values, as well as with reference to the zero line contour separating the shaded from unshaded regions. While each of these six patient-specific maps were generated using intracardiac pacing, naturally occurring ectopic origins may be identified by comparing reference heart cycle signals measured during premature atrial beats, the onset of AFib, and/or atrial tachycardia (and optionally separated from superimposed signals described above) to these mean paced plots.

Referring now to FIGS. 7 and 8, a right ventricular database 82 and a left ventricular database 84 each include mean QRS integral maps for paced ectopic origins in the right and left ventricles, respectively. These ventricular databases are more fully described in an article by Peeters, H. A. P. et al. entitled "Clinical Application of an Integrated 3-Phase Mapping Technique for Localization of the Site of Origin of Idiopathic Ventricular Tachyardia", *Circulation* 99:1300–1311 (1999) the disclosure of which is incorporated herein by reference.

Figure 9:
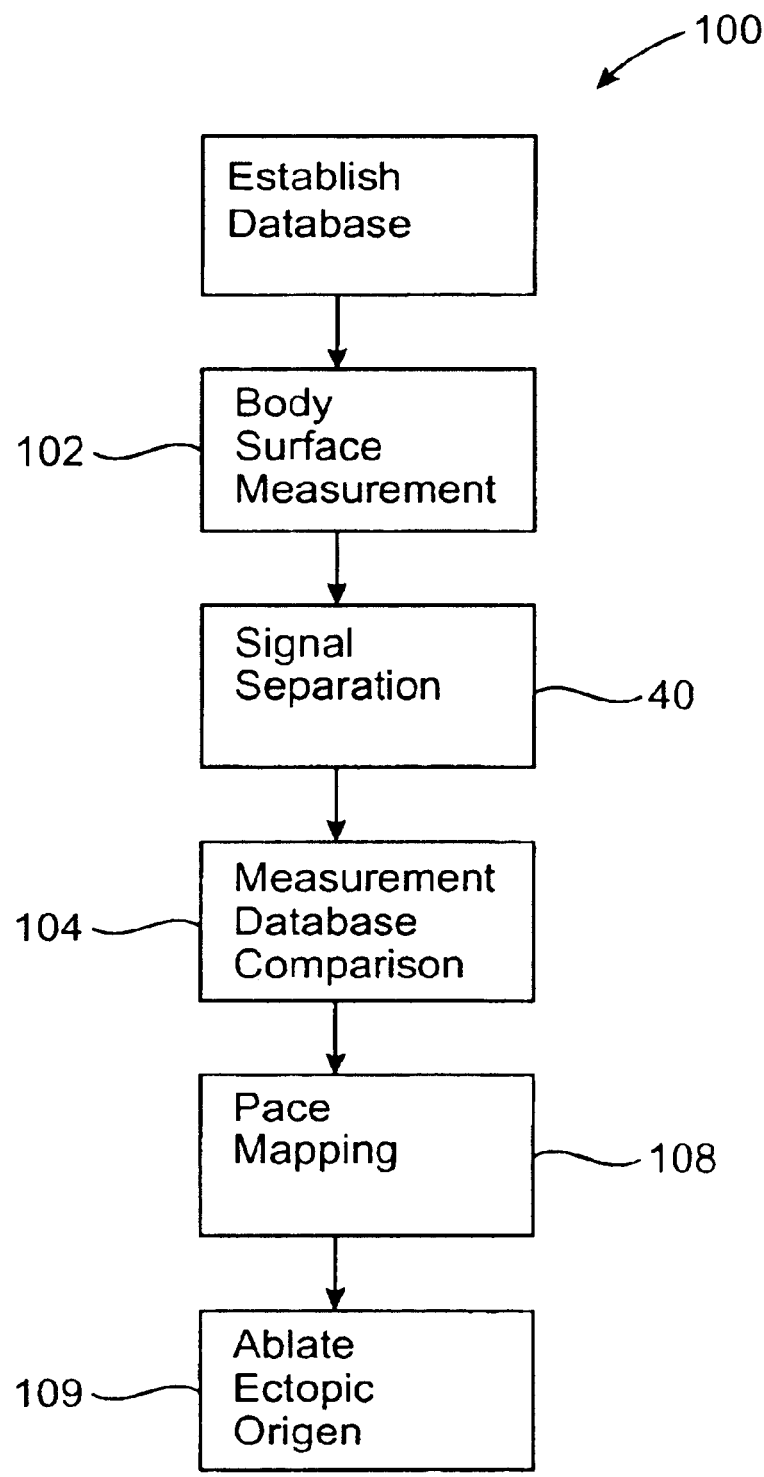
FIG. 9 illustrates a diagnosis and treatment methodology using an arrhythmia location database and signal separator to help locate and treat the origins of focal AFib and other arrhythmias.

Referring now to FIG. 9, a localization/treatment method 100 may be performed by first establishing a database of arrhythmogenic regions and associated heart cycle signal characteristics, as described with reference to FIGS. 4A–8 above. Body surface measurements are taken in step 102, typically using sensor array 10 described with reference to FIG. 1A. As the P wave will often overlap other heart signal portions, localization of AFib and other arrhythmias will benefit from a signal separation program as described above regarding FIGS. 2–3D.

Once signal separation has been effected, P wave integrals (or other selected indicia) are determined for each sensor 12, and data matrices assembled as described with reference to FIGS. 1B and 1C. Once again, it should be understood that these P wave integrals are calculated for a reference heart cycle signal of interest, usually for a premature atrial beat or for the heart cycle signal at the onset of an arrhythmia, for focal arrhythmias. Optionally, the data matrix may be compared with the plots of the established database in step 104. This database comparison method may simply involve visually selecting the mean-paced integral map which appears most similar to the plot for a specific patient. Alternatively, statistical correlation coefficients may be generated between the data matrix for the patient and each of the mean-paced groups of the database. In some embodiments, different patient plots may be prepared for comparison with different databases, for example, a P wave integral may be calculated for comparison with atrial database groups, while a QRS integral plot may be prepared for comparison with ventricular database groups.

Figure 9A:
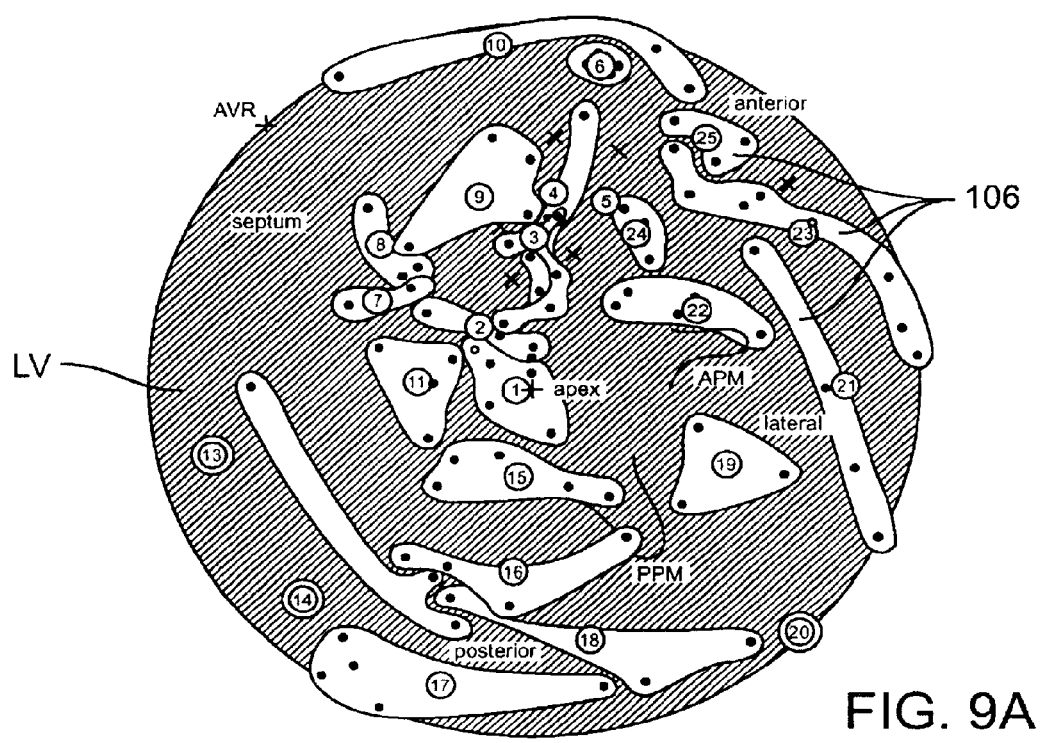
FIGS. 9A and 9B illustrate arrhythmogenic regions of the left and right ventricles, respectively.
Figure 9B:
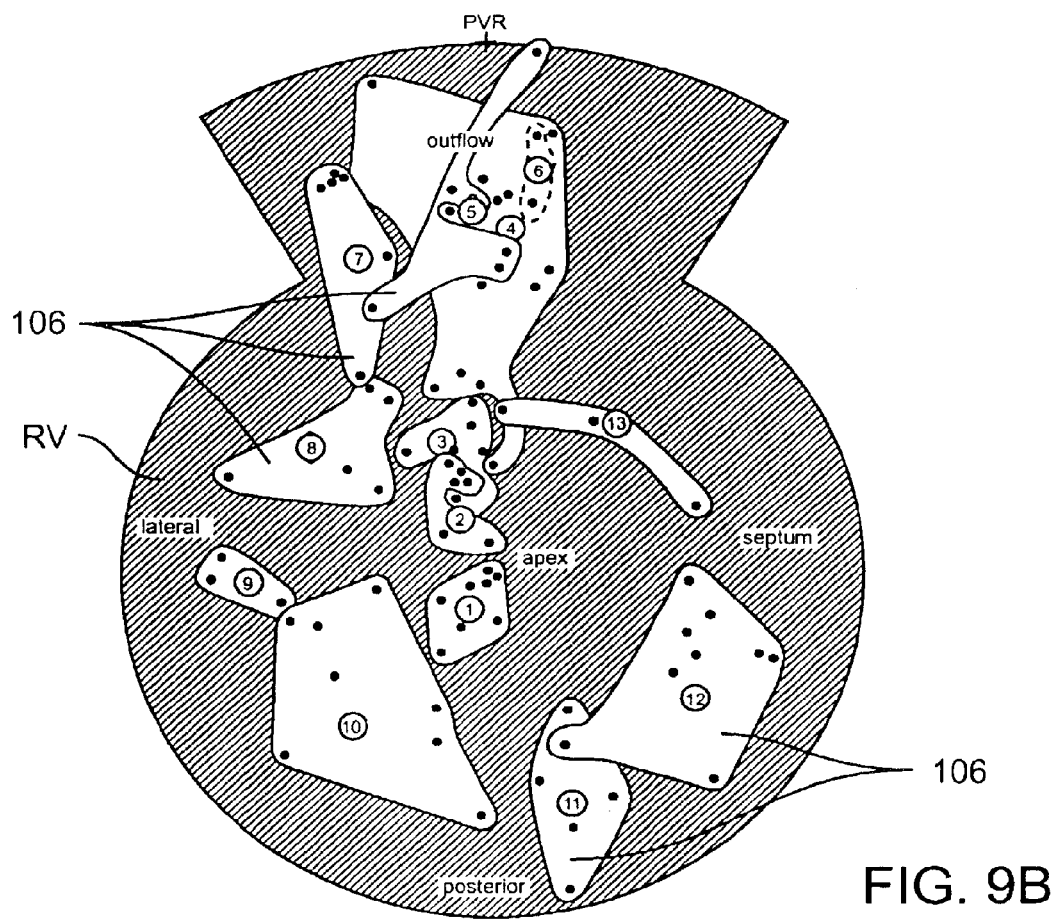

Once a mean-paced integral plot from the database has been selected as the closest correlation to the reference cycled plot for a particular patient, an arrhythmogenic region 106 associated with the corresponding mean-paced plot has effectively been identified. Arrhythmogenic regions 106 associated with mean-paced plots 1–25 of left ventricular database 84 and plots 1–13 of right ventricular database 82 are illustrated in FIGS. 9A and 9B, respectively. In many embodiments, these arrhythmogenic regions will be discrete locations based on the information within the associated database. Preferably, arrhythmogenic regions 106 will have surface areas of less than about 5 cm². Optionally, the arrhythmogenic regions may have an outer radius which is less than about 2.5 cm, ideally about 1.0 cm or less. In some embodiments, the arrhythmogenic regions identified by sensor array 10 on the patient's torso may be small enough that no further localization is needed, and ablation of the ectopic site or exit site within the arrhythmogenic region may proceed without excessive collateral damage.

Figure 10:
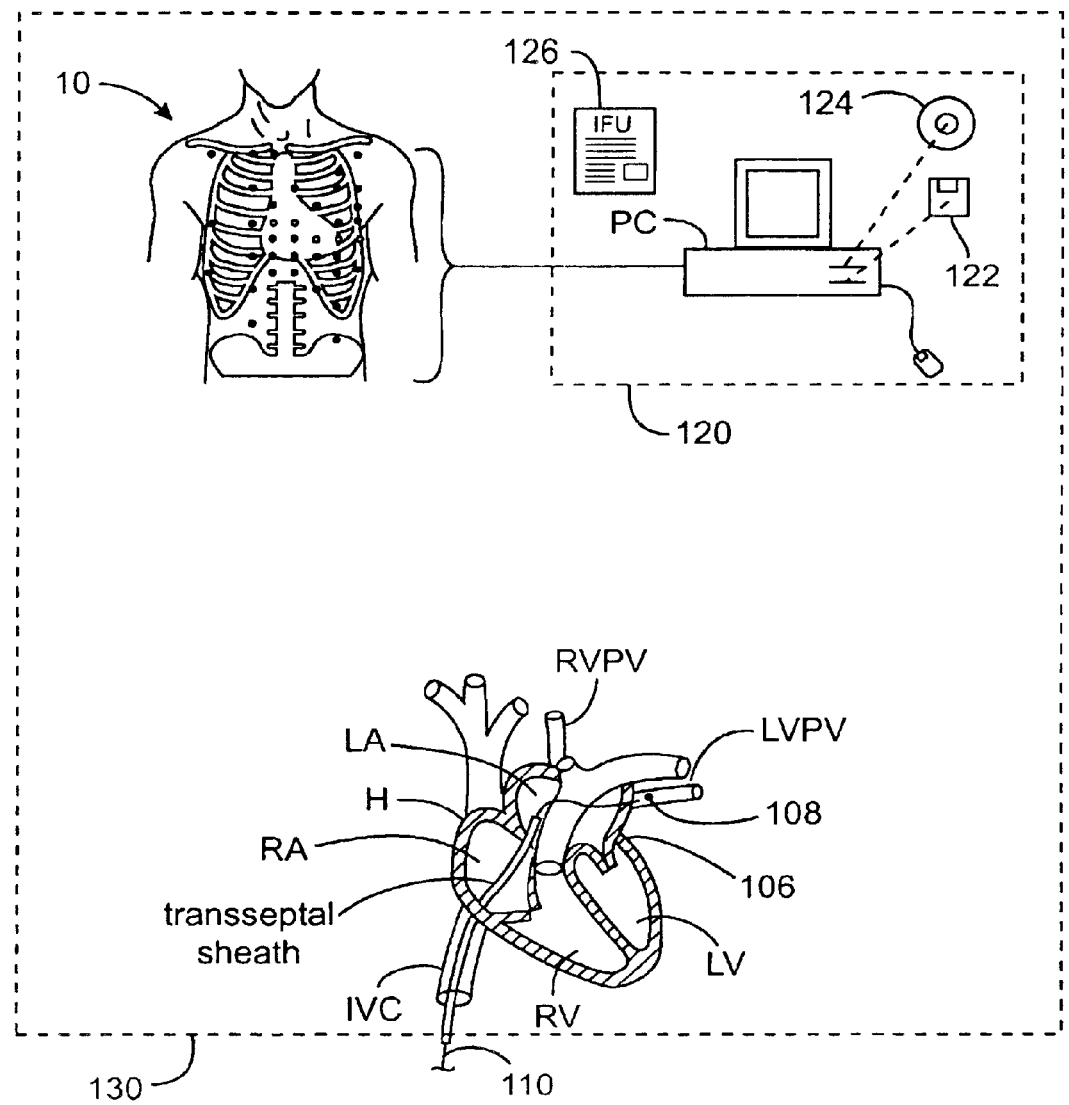
FIG. 10 schematically illustrates a system and/or kit for diagnosing and/or treating focal AFib and other arrhythmias, according to the principles of the present invention.
Figures 11A, 11B:
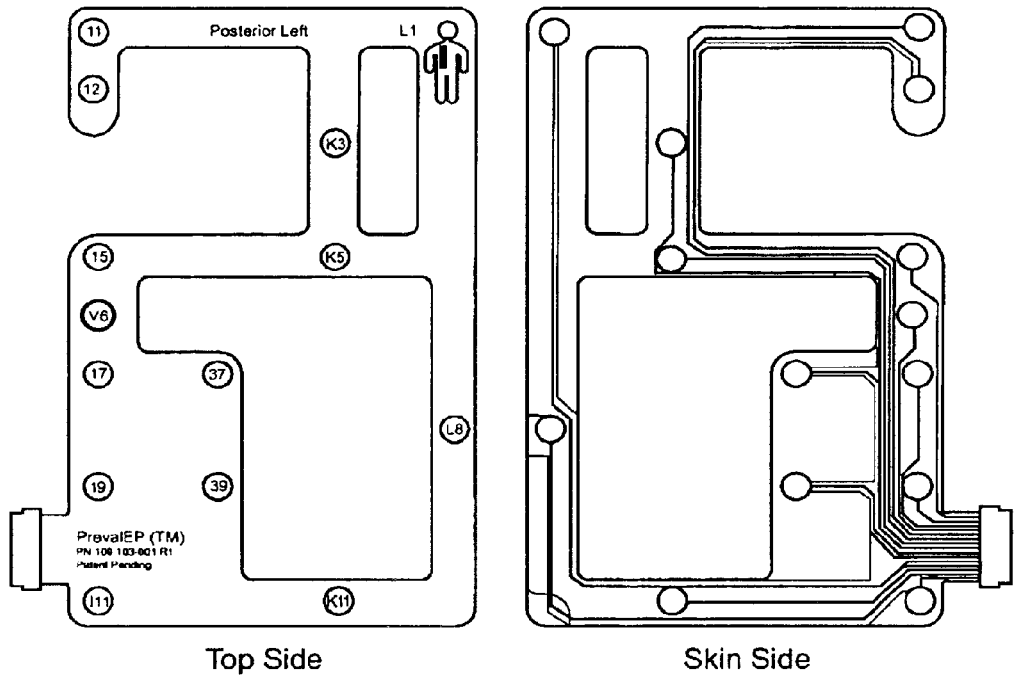
FIGS. 11A–11H illustrate exposed and skin-engaging surfaces of four panels supporting heart cycle sensors in an exemplary sensor array structure.
Figures 11C, 11D:
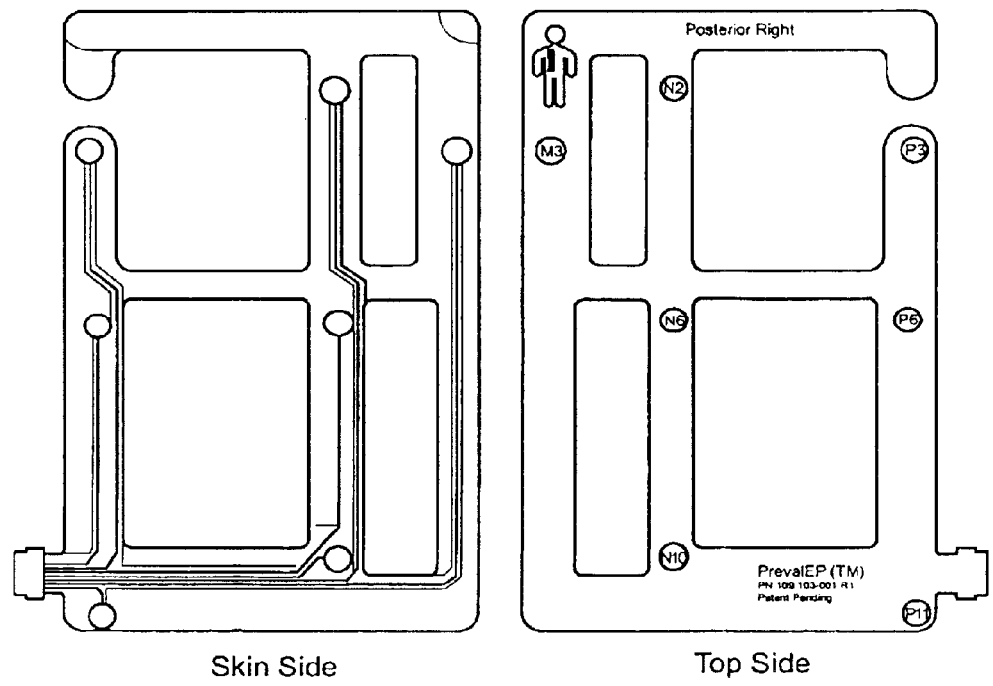
Figure 11E:
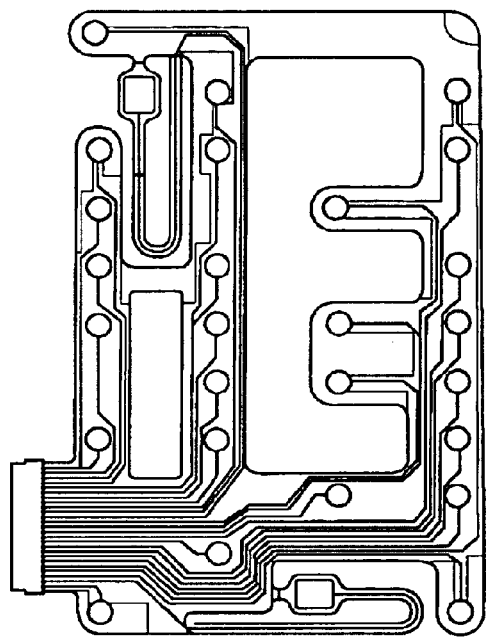
Figure 11F:
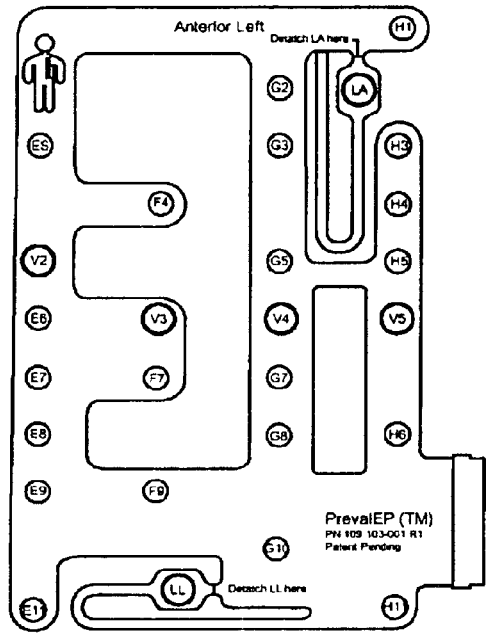
Figure 11G:
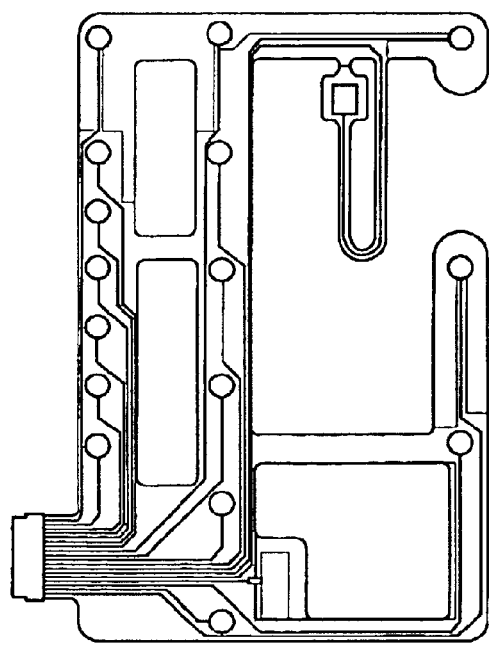
Figure 11H:
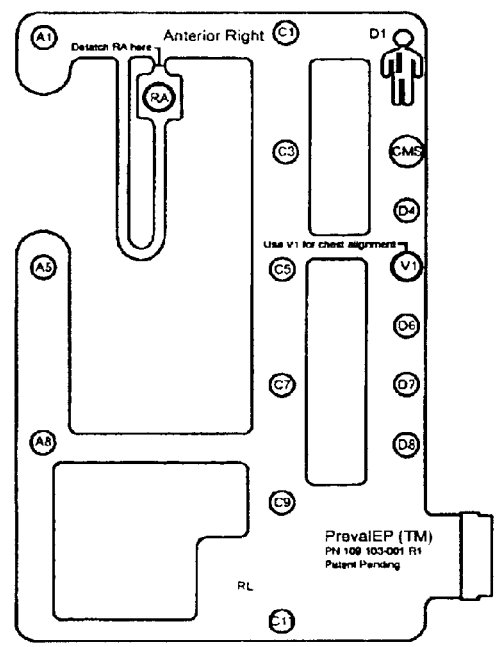

Referring now to FIGS. 9 and 10, once an arrhythmogenic region 106 has been identified, it will often be advantageous to further localize an ectopic origin or exit site 108 within arrhythmogenic region 106 using a pace mapping catheter 110. Advantageously, this mapping of ectopic origin or exit site 108 may proceed rapidly within the limited confines of the arrhythmogenic region 106, thereby reducing fluoroscopy time and radiation exposure to patient and attending personnel, decreasing the trauma associated with accessing alternative portions of heart H, and the like. In general, pace mapping is effected by electrical stimulation of candidate ectopic origins within arrhythmogenic region 106 using a distal electrode pair of catheter 110. This can induce ectopic heart beats which can also be measured by array 10 (or a similar array adapted for use in a high electromagnetic noise environment). Positioning of the catheter tip may be monitored using biplane x-ray imaging.

The surface ECG corresponding to the paced beats is recorded, and the desired integrals and associated data matrix is generated, as described above. By comparing the data matrix plot of the induced arrhythmia to the database and/or original arrhythmia recordings, the focal origin or exit site of the arrhythmia relative to the catheter position can be estimated, optionally using the method described in U.S. Pat. No. 5,311,873, previously incorporated herein by reference. The catheter may be moved to the indicated alternative site, and the pacing and measurement steps repeated iteratively until the ectopic site is found where the paced data matrix plot best correlates with the data matrix plot of the arrhythmia. Once again, this iterative process is greatly expedited by concentrating the ectopic origin or exit site search within arrhythmogenic region 106 identified using sensor array 10.

Once the ectopic origin or exit site has been sufficiently localized, ablation of the ectopic origin 109 is effected, often using an ablation electrode of pacing catheter 110. A variety of alternative tissue treatment modalities might be applied to the ectopic origin or exit site, including radiofrequency ablation, cryogenic cooling, ultrasound, laser, microwave, bioactive agents, and the like. Similarly, a variety of intra-cardiac localization techniques might be used in place of intracardiac pace mapping 108 under fluoroscopy. Suitable three-dimensional electro-anatomical point-by-point mapping systems may be commercially available for localization of an ectopic origin or exit site within an arrhythmogenic region from BIOSENSE-WEBSTER, INC. under the trademark CARTO®, and a related Real-Time Position Management™ system may be available from CARDIAC PATHWAYS CORPORATION. Alternative multi-electrode catheters may be commercially available from CARDIMA, INC., BIOSENSE-WEBSTER, INC., CARDIAC PATHWAYS CORPORATION, BARD, INC. and/or EP TECHNOLOGIES, INC. A still further alternative for localizing of the ectopic origin within an arrhythmogenic region maybe provided using a three-dimensional non-contact multi-electrode mapping system under development by ENDOCARDIAL SOLUTIONS, INC. Mapping/ablation catheters may also be available from both ENDOCARDIAL SOLUTIONS, INC. and CARDIMA, INC. Exemplary cryogenic systems may be available from CRYOCATH, INC. and from CRYOGEN, INC. A suitable cooled radiofrequency ablation catheter is sold commercially as the CHILLI®-Cooled Ablation System from CARDIAC PATHWAYS CORPORATION. Pulmonary vein isolation systems for use with the invention are now being developed by ATRIONIX (ultrasound) and CARDIOFOCUS (laser ablation).

Referring to FIG. 10, a kit 120 for localization of an arrhythmogenic region of heart H may include a tangible media having a machine-readable code embodying any of the methods described herein above. Media 122 will often be used in a general-purpose computer PC coupleable to array 10, with the PC typically having a processor for effecting the method steps embodied in media 122, as well as input devices such as a mouse, keyboard, an Internet, Ethernet, and/or Intranet, as well as output devices such as monitor, a printer, an I/O port, and/or the like. The PC will often manipulate the data in response to heart cycle signals sensed by array 10, and also in response to a heart cycle signal database 124, as described herein above. Instructions for use 126 will often be included within kit 120, with the instructions and at least one other component of the kit often being packaged together, instructions for use 126 optionally being embodied as printed information (optionally appearing at least in part on the packing material), a VCR tape, media embodying a machine readable code, or the like.

In many embodiments a system 130 will include one or more components of kit 120, and may also include array 10 and/or a probe such as catheter 110 for localization and/or treatment of the arrhythmias.

In some embodiments, continuous localization of local triggers or exit sites may be provided using correlations such as those described in an article by Potse, M. et al., entitled "Continuous Localization of Cardiac Activation Sites Using a Database of Multichannel ECG Recordings," *IEEE Trans. Biomed. Eng.*, 47:682–689 (2000), the full disclosure of which is incorporated herein by reference.

FIGS. 11A–H illustrate skin-engaging and outer surfaces of four flexible sensor panels. These panel structures and the use of their array or sensors are more fully described in U.S. patent application Ser. No. 09/611,179, filed on Jul. 6, 2000, the disclosure of which is incorporated herein by reference.

Figure 12A:
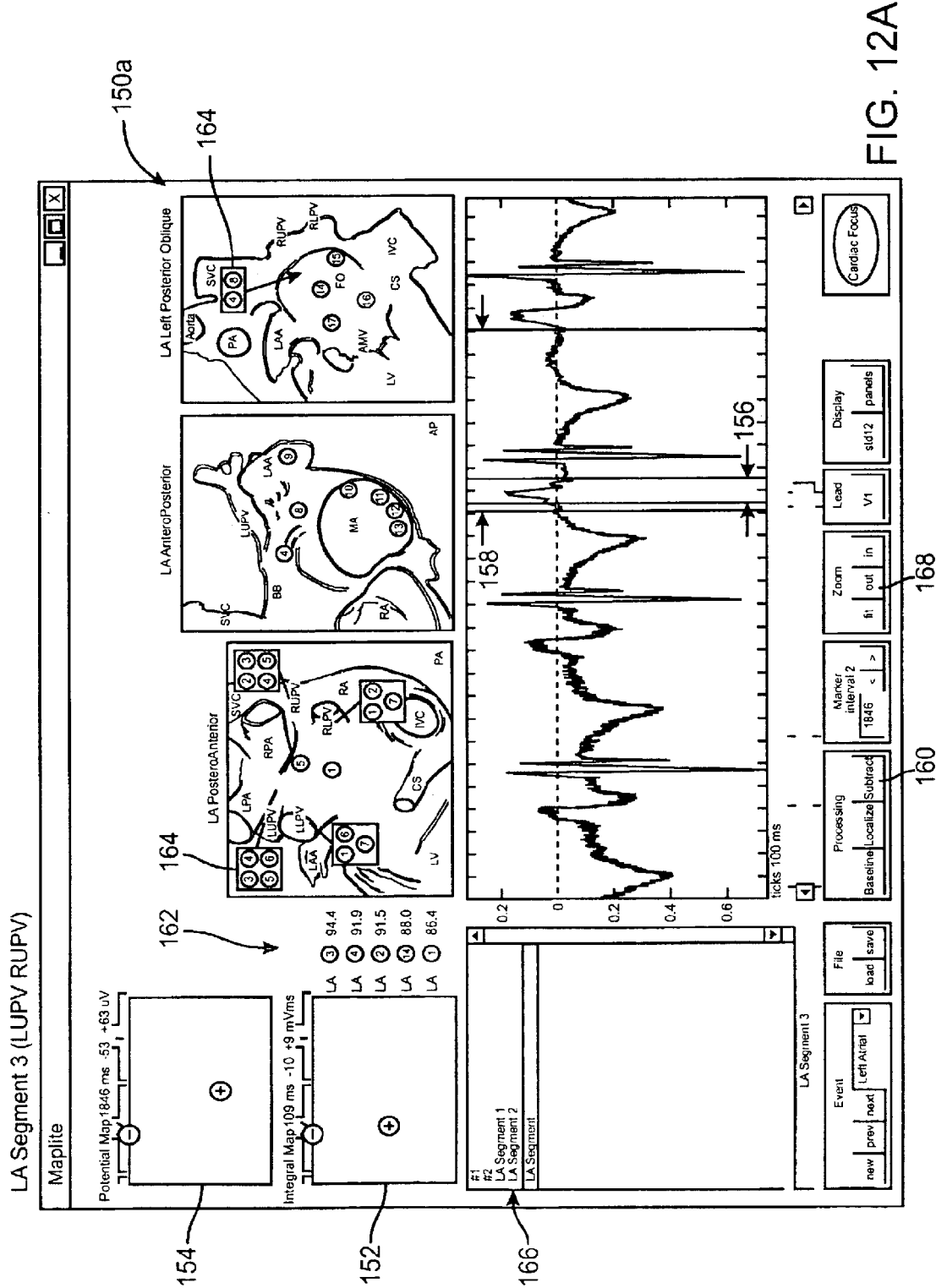
FIGS. 12A and 12B are computer screen prints of an AFib localization program showing the localization output.
Figure 12B:
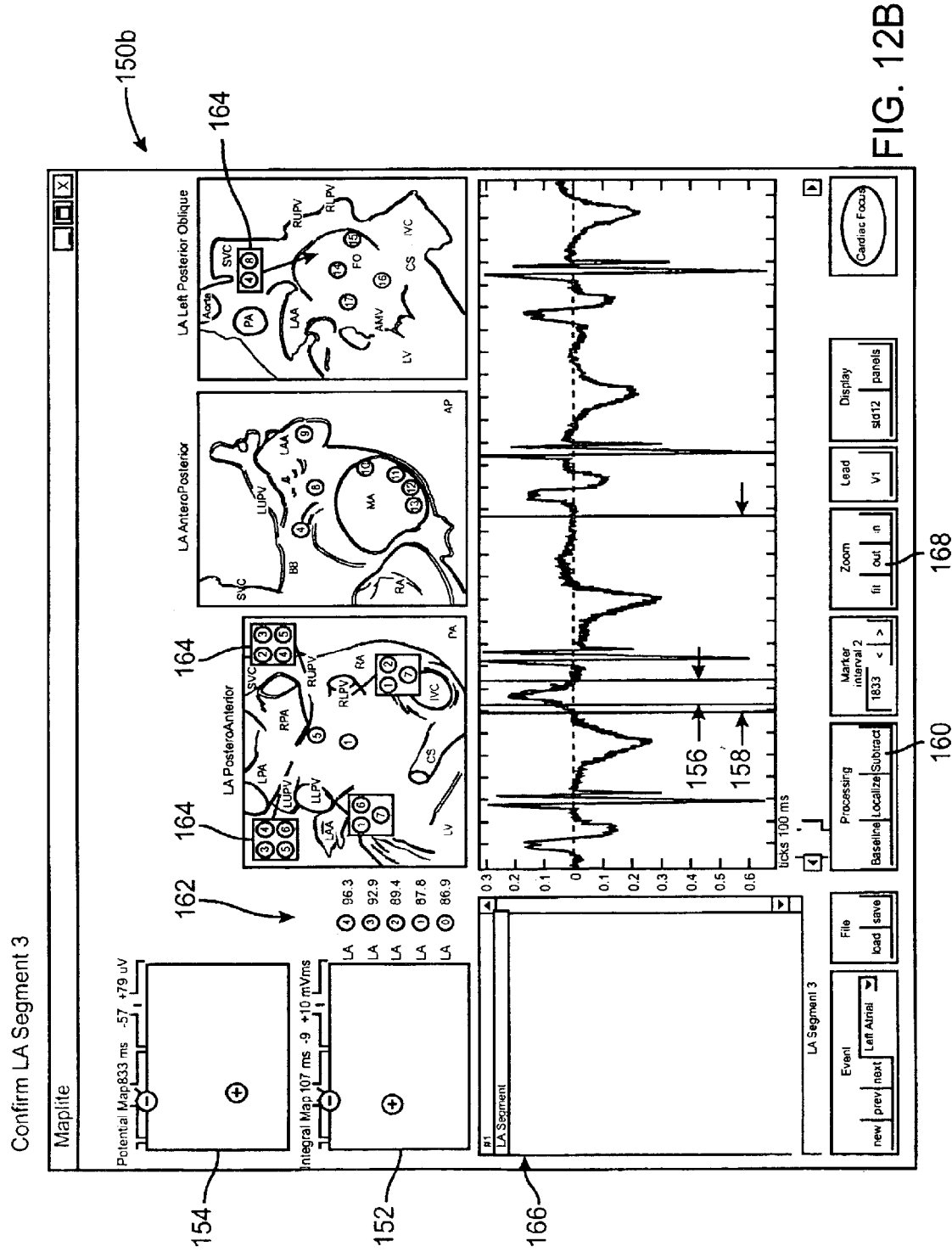

Referring now to FIGS. 12A and 12B, screen prints 150a, 150b are at least a portion of the output of a localization computer program as described herein. Integral maps 152 are multi-color graphical representations of the morphology derived from body surface potential maps 154 (also displayed in a multi-color format). Time portion 156 of reference cycle 158 is shown graphically, and may be separated from a superimposed signal by inputting a "subtract" command 160, ideally using a graphical user interface. Identified arrhythmogenic sites 12 are output with their associated probabilities, and are graphically illustrated 164 relative to the adjacent anatomy. In the exemplary output, candidate sites of a selected database are also shown, with one or more of the identified sites being highlighted using color, blinking, an enhanced font or icon, or the like. Optionally, cycle signals from different recorded segments 166 may be selected, and the cycles of interest may be time scaled or zoomed 168 to show the desired cycle intervals. Signals from selected leaps or sensor panels may be displayed, and a variety of additional outputs may be provided. In the output illustrated in screen prints 150a, 150b, two different reference cycles from different arrhythmia events result in similar identified arrhythmogenic sites. Hence, the present invention can also provide confirmation of an arrhythmogenic site identification from one or more confirmation reference cycle.

While the exemplary embodiments have been described in some detail, by way of example and for clarity of understanding, a variety of changes, adaptations, and modifications will be obvious to those of skill in the art. Hence, the scope of the present invention is limited solely by the appended claims.

What is claimed is:

1. A method for treating fibrillation in a heart of a patient, the patient having an external body surface, the method comprising;
measuring the fibrillation from the body surface by sensing heart cycle signals while no intracardiac probe is present in the heart;
locating an arrhythmogenic region of the heart in response to the measured fibrillation such that the arrhythmogenic region is determined using the sensed heart cycle signals prior to intracardiac access; and
directing treatment at or near the arrhythmogenic region so that the fibrillation is inhibited.

2. The method of claim 1, further comprising sensing the heart cycle signals with a two-dimensional array of sensors while the sensor array is coupled to thoracic skin of the patient, the array having more than 20 sensing locations.

3. The method of claim 1, the heart cycle signals including an atrial signal superimposed with a ventricular signal, the atrial and ventricular signals being separable by a signal separator, further comprising separating the atrial and ventricular signal with the signal separator.

4. The method of claim 3, further comprising selecting at least one reference cycle from among a plurality of heart cycles, wherein the arrhythmogenic region is determined at least in part from the separated heart cycle signals during the at least one reference cycle.

5. The method of claim 4, further comprising selecting a time portion of the at learnt one reference cycle and comparing separated signals from an array of sensing location during the selected time portion.

6. The method of claim 5, further comprising generating a data matrix by integrating the separated atrial signals, the separated atrial signals comprising potential value signals from each sensor location, the separated atrial signal for each associated sensor location integrated within the selected time portion so as to define an integral value, and arranging the integral values within the matrix according to locations of the associated sensor locations along the body surface.

7. The method of claim 6, further comprising graphically plotting the data matrix, determining lines of constant integral values along the plots, and identifying the arrhythmogenic region within an atrium of the heart using the lines of constant integral values.

8. The method of claim 3, a database having a plurality of known cycles, each known cycle having an associated known arrhythmogenic region, and further comprising comparing the signals during the at least one reference cycle to the known cycles of the database.

9. The method of claim 1, wherein the locating step comprises identifying an atrium having the arrhythmogenic region from among a left atrium and a right atrium of the heart of the patient with the measured fibrillation.

10. The method of claim 9, wherein the locating step is performed so that the located arrhythmogenic region barn a surface area of less than about 5 cm$^2$.

11. The method of claim 9, wherein the locating step is performed so that an outer radius of the arrhythmogenic region is less than about 2.5 cm.

12. The method of claim 9, wherein the locating step is performed so that an outer radius of the arrhythmogenic region is about 1.5 cm or less.

13. The method of claim 1, further comprising introducing a probe into an atrium alter locating the arrhythmogenic region within the atrium and identifying an ectopic site or exit site with the probe.

14. The method of claim 13, wherein the probe comprises a pacing probe, and further comprising initialing an artificial arrhythmia by stimulating a candidate ectopic site within the arrhythmogenic region using the probe and comparing heart cycle signals from the artificial arrhythmia with the sensed signals.

15. The method of claim 1, wherein the directing step comprises ablating at or near an ectopic site or exit site.

16. A method for treating arrhythmia in a heart of a patient, the patient having an accessible body surface, the heart having a left atrium, a left ventricle, a right atrium, and a right ventricle, heart signals at the body surface including atria signals superimposed with ventricular signals, the atrial and ventricular signals being separable by a signal separator, a database having information regarding a plurality of known cycles, each known cycle having an associated known arrhythmogenic region, the method comprising:
sensing signals during an arrhythmia-initiation cycle or an atrial premature beat cycle from the body surface;
separating the atrial signals from the sensed signals with the signal separator;
locating an arrhythmogenic region of an arrhythmogenic atrium of the heart prior to any introduction of a cardiac probe into the heart by comparing the separated signals to the database; and
directing a treatment at or near an ectopic site or an exit site within the arrhythmogenic region so that the arrhythmia is inhibited.

17. A system for treating arrhythmia in a heart of a patient, the patient having an exposed body surface and the heart having an atrium and a ventricle, wherein a sensor array is coupled to the body surface for sensing heart cycle signals, the heart signals including atrial signals superimposed with ventricular signals, the atrial and ventricular signals being separable by a signal separator, and wherein a database has information regarding a plurality of known cycles, each known cycle having an associated known arrhythmogenic region, the system comprising:
a processor coupled to the database, the processor deriving an arrhythmogenic region of the atrium from the heart cycle signals by separating the atrial or ventricular signals with the signal separator and comparing the separated signals to the database; and
a probe for directing treatment at or near an ectopic origin or exit site within the arrhythmogenic region so that the arrhythmia is inhibited.

18. The system of claim 17, the sensor array having an array of sensors and defining an array of sensor locations, wherein the processor stores at least one reference cycle from among a plurality of heart cycles and a selected time portion of the at least one reference cycle, and wherein the processor is configured to locate the arrhythmogenic region by comparing the separated signals from the array of sensing locations during the selected time portion by integrating a potential value of the separated atrial signals from each sensor location within the selected time portion so as to define an integral value, and arranging the integral values within a data matrix according to associated sensor locations along the body surface.

19. A method for treating fibrillation in a heart of a patient, the patient having an accessible body surface, the method comprising:

measuring the fibrillation from the body surface by sensing heart cycle signals at an array of sensing locations while no intracardiac probe is present in the heart, the heart cycle signals including an atrial signal superimposed with a ventricular signal;

selecting at least one reference cycle from among a plurality of heart cycles;

locating an arrhythmogenic region of the heart in response to the measured fibrillation by:

selecting a time portion of the at least one reference cycle;

separating the atrial and ventricular signals with a signal separator, and comparing the separated signals from the array of sensing locations during the selected time portion by integrating a potential value of the separated signals from each sensor location within the selected time portion so as to define an integral value, and arranging the integral value within a data matrix according to associated sensor locations along the body surface; and directing treatment at or near the arrhythmogenic region so that the fibrillation is inhibited.

20. The method of claim 19, further comprising sensing the heart cycle signals with an ray of signals while the sensor stray is coupled to thoracic skin of the patient, the array having more than 20 sensing locations.

21. The method of claim 19, further comprising graphically plotting the data matrix, determining lines of constant integral values along the plots, and identifying the arrhythmogenic region within an atrium of the heart using the lines of constant integral values.

22. The method of claim 19, a database having a plurality of known cycles, each known cycle having an associated known arrhythmogenic region, and further comprising comparing the signals during the at least one reference cycle to the known cycles of the database.

23. The method of claim 19, wherein the locating step comprises identifying an atrium having the arrhythmogenic region from among a left atrium and a right atrium of the heart of the patient with the measured fibrillation.

24. The method of claim 23, wherein the locating step is performed so that the located arrhythmogenic region has a surface area of less than about 5 $cm^2$.

25. The method of claim 23, wherein the locating step is perform so that an outer radius of the arrhythmogenic region is less than about 2.5 cm.

26. The method of claim 23, wherein the locating step is performed so that an outer radius of the arrhythmogenic region is about 1.5 cm or less.

27. The method of claim 19, further comprising introducing a probe into an atrium after locating the arrhythmogenic region within the atrium and identifying an ectopic site or exit site with the probe.

28. The method of claim 27, wherein the probe comprises a pacing probe, and further comprising initiating an artificial arrhythmia by stimulating a candidate ectopic site within the arrhythmogenic region using the probe and comparing heart cycle signals from the artificial arrhythmia with the sensed signals.

29. The method of claim 19, wherein the directing step comprises ablating at or near an ectopic site or exit site.

* * * * *